(12) United States Patent
Song et al.

(10) Patent No.: US 9,181,193 B2
(45) Date of Patent: Nov. 10, 2015

(54) INDENOQUINOLONE COMPOUND, PREPARATION METHOD AND USE THEREOF

(75) Inventors: Yunlong Song, Shanghai (CN); Xiaodan Fu, Shanghai (CN); Yunpeng Qi, Shanghai (CN); Yves G. Pommier, Bethesda, MD (US)

(73) Assignee: Second Military Medical University, PLA, Shanghai (CN)

( * ) Notice: Subject to any disclaimer, the term of this patent is extended or adjusted under 35 U.S.C. 154(b) by 0 days.

(21) Appl. No.: 13/698,739

(22) PCT Filed: May 17, 2011

(86) PCT No.: PCT/CN2011/074203
§ 371 (c)(1), (2), (4) Date: Dec. 19, 2012

(87) PCT Pub. No.: WO2011/144020
PCT Pub. Date: Nov. 24, 2011

(65) Prior Publication Data
US 2013/0102598 A1 Apr. 25, 2013

(30) Foreign Application Priority Data
May 17, 2010 (CN) .......................... 2010 1 0176288

(51) Int. Cl.
| | |
|---|---|
| A61K 31/44 | (2006.01) |
| C07D 221/18 | (2006.01) |
| C07D 221/22 | (2006.01) |
| C07D 401/12 | (2006.01) |
| C07D 413/12 | (2006.01) |
| C07D 401/06 | (2006.01) |
| A61K 9/48 | (2006.01) |

(52) U.S. Cl.
CPC ............ *C07D 221/18* (2013.01); *A61K 9/4858* (2013.01); *A61K 9/4866* (2013.01); *C07D 401/06* (2013.01); *C07D 401/12* (2013.01); *C07D 413/12* (2013.01)

(58) Field of Classification Search
None
See application file for complete search history.

(56) References Cited

U.S. PATENT DOCUMENTS 7,829,567 B2 * 11/2010 Tzeng et al. ............. 514/253.02
2009/0111987 A1   4/2009 Tzeng et al.

FOREIGN PATENT DOCUMENTS

| CN | 1780624 | 5/2006 |
|---|---|---|
| CN | 101565402 | 10/2009 |
| JP | 9143166 | 6/1997 |
| JP | 3643916 B2 * | 4/2005 |
| WO | 93/05023 | 3/1993 |
| WO | WO 93/05023 A * | 3/1993 |
| WO | 2004/014862 | 2/2004 |
| WO | 2007/059008 | 5/2007 |
| WO | WO 2007/059008 A2 * | 5/2007 |

OTHER PUBLICATIONS

Tseng, CH. et al. Synthesis and antiproliferative evaluation of certain indeno[1,2-c]quinoline derivatives. Bioorganic & Medicinal Chemistry, vol. 16, p. 3162.*
Brooks, LR. et al. Bioassay-Directed Fractionation and Chemical Identification of Mutagens in Bioremediated Soils. Environmental Health Perspectives. 1998, vol. 106, p. 1439.*
Mahmoud, MR. et al. Synthesis and reactions of indeno[1,2-c]chromene-6,11-dione derivatives. Journal of Chemical Research. 2008, vol. 11, p. 609.*
Mahmoud, MR. et al. Synthesis and reactions of indeno[1,2-c]chromene-6,11-dione derivatives. Journal of Chemical Research. 2008, vol. 11, p. 611.*
Greenwald, RB. et al. Drug Delivery Systems: Water Soluble Taxol 2'-Poly(ethylene glycol) Ester Prodrugs-Design and in Vivo Effectiveness. J. Med. Chem. 1996, vol. 39, p. 425.*
Testa, B. et al. Lessons Learned from Marketed and Investigational Prodrugs. J. Med. Chem. 2004, vol. 47(10), p. 2393.*
International search report for international application No. PCT/CN2011/074203, dated Aug. 25, 2011 (10 pages).

(Continued)

*Primary Examiner* — Rita Desai
*Assistant Examiner* — Ben S Michelson
(74) *Attorney, Agent, or Firm* — Hamre, Schumann, Mueller & Larson, P.C.

(57) ABSTRACT

An indenoquinolone compounds of Formula (A) is disclosed, wherein the definition of each group is described in the description. These compounds may specifically inhibit topoisomerase I, and they have good activities against many kinds of human tumor cells, such as lung cancer, colon cancer, breast cancer, liver cancer and the like. They can be used in the manufacture of antitumor drugs. The method for preparing the compound of formula (A), and pharmaceutical compositions containing such compounds and the use in the manufacture of antitumor drugs are also disclosed.

(A)

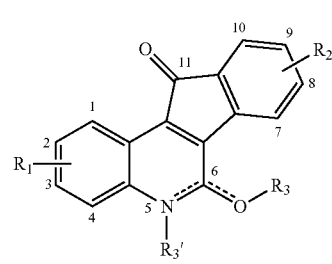

8 Claims, No Drawings

(56) References Cited

OTHER PUBLICATIONS

Chih-Hua Tseng et al., "Synthesis and antiproliferative evaluation of 6-arylindeno[1,2-c]quinoline derivatives," Bioorganic & Medicinal Chemistry 17 (2009) p. 7465-7476.
Chih-Hua Tseng et al., "Synthesis and antiproliferative evaluation of certain ideno[1, 2-c]quinoline derivatives," Bioorganic & Medicinal Chemistry 16 (2008) p. 3153-3162.

A. Morrell et al., "Nitrated Indenoisoquinolines as Topoisomerase I Inhibitors: A Systematic Study and Optimization," J. Med. Chem., 2007, vol. 50, p. 4419-4430.
S. Antony et al., "Novel Indenoisoquinolines NSC 725776 and NSC 724998 Produce Persistent Topoisomerase I Cleavage Complexes and Overcome Multidrug Resistance," Cancer Res, 2007, vol. 67, p. 10397-10405.

* cited by examiner

INDENOQUINOLONE COMPOUND, PREPARATION METHOD AND USE THEREOF

TECHNICAL FIELD

The present invention relates to the field of pharmaceutical technology, more specifically, to a series of indenoquinolone compounds. The present invention also relates to compositions containing these compounds, preparation method and use of these compounds in the preparation of anticancer, antifungal, and antiviral medicaments.

BACKGROUND ART

Malignancy is one of the major diseases that seriously threaten the human life and the quality of life. In recent years, chemotherapy has made considerable progress, significantly prolonged the survival of cancer patients, and in particular, made significant breakthroughs in the treatment of leukemia, malignant lymphoma. However, satisfactory results in treating solid tumors (including lung cancer, liver cancer, bladder cancer, and colon cancer, etc.), which most seriously endanger human life and health, and account for more than 90% of the malignancies, have not been achieved.

With the rapid developments in the life sciences, tumor mechanism has been gradually clarified, new ideas have appeared successively, such as inhibiting tumor growth factor, intervening cancer signaling, inhibiting tumor angiogenesis, and inducing tumor cell apoptosis. However, since the pathogenesis of malignant tumors is very complex, clinical practice in recent years has shown that the better clinical efficacy can be achieved only by using them in the combination with cytotoxic medicaments. Therefore, it is of great significance to use key enzymes relevant to the proliferation and differentiation in the tumor cells as a drug target for developing novel medicaments which have high efficiencies, low toxicities as well as strong specificities, and can selectively act on specific target(s).

Topoisomerase I (Top1) has become one of the key target enzymes for designing novel anti-cancer medicaments. The enzyme is necessary for cell survival and involves in the whole procedure of DNA replication, transcription, recombination, and repair; and the Top1 content in a variety of tumor cells, especially lung cancer, stomach cancer, colon cancer, and ovarian cancer, etc., is significantly higher than that in normal cells. Therefore, Top1 inhibitors have not only high efficacies and broad anti-tumor spectra, but also good selectivities for tumor cells. The Top1 inhibitors have been classified as one of six categories of key anticancer medicaments by the U.S. National Cancer Institute.

In all kinds of Top1 inhibitors, camptothecin (CPT) compounds, the most classical Top1-specific inhibitor, have been studied most deeply and become one highlight of the anticancer medicaments research in recent years. In these compounds, Irinotecan (CPT-11) and Topotecan have been successfully marketed, used for the treatment of metastatic colorectal cancer and refractory ovarian cancer etc., and achieved good efficacies. Therefore, the camptothecin derivatives, paclitaxel and retinoic acid compounds have been praised as the three major findings of anti-cancer medicaments in the 1990s. However, such compounds also have prominent problems as follows: 1) the metabolically labile in vivo, that is, the E-ring lactone structure necessary for activity is hydrolyzed into a carboxylic acid salt form in the human body very quickly, and the form of carboxylic acid salt is not only ineffective to Top1, but also more likely to bind human serum albumin; 2) Top1 cleavable-complex (Top1cc) need to be maintained relatively long time to be converted into DNA damage. However, camptothecins tend to dissociate from Top1cc, therefore, the period for intravenous dripping must be prolonged when the camptothecin medicaments are used in clinic; 3) camptothecin possesses strong hydrophobicity due to the unique five-ring conjugated planar structure, resulting in poor water solubility; 4) camptothecins have certain toxic side effects, such as leukopenia, nausea, vomiting, etc., thus restricting the safe dose and in turn the efficacy; 5) resistance. At present, several camptothecin resistant Top1 mutants have been reported. The most frequent mutations, such as Asn722, Arg364, etc., can result in the resistance to camptothecin.

Recently, non-camptothecin Top1 inhibitors have become the hotspot in the research of anti-cancer medicaments. Indolocarbazole compounds are studied deeply at present, wherein, J-107088 (Edotecarin) has entered into the clinical study. However, studies have shown that these compounds are not specific Top1 inhibitors, and also have the inhibitory activity for protein kinase C or checkpoint kinase Chk-1. Luotonine A and Lamellarin D are also Top1 inhibitors isolated from nature in recent years, but they have defects, such as complex structures, poor specificities, and high toxicities. At present only camptothecin anti-tumor medicaments are used widely in clinical practice.

In non-camptothecin Top1 inhibitors, indenoisoquinoline compounds increasingly attracted people's attention. In these compounds, NSC 314622 was initially synthesized by Cushman group (Purdue University) in 1978 and was found to have strong anti-tumor activity. However, its mechanism of action remains unclear. Until 1998, Pommier et al of NCI found that Top1 is the target site of indenoisoquinoline antitumor compounds. This result promoted the in-depth study of such compounds. Cooperated with NCI, Cushman group synthesized four to five hundred indenoisoquinoline compounds, comprehensively studied these compounds for their Top1 inhibitory effect as well as the anti-tumor activities, elucidated the structure-activity relationship of these compounds and obtained the crystal structure of one such compound with Top1-DNA covalent complex. Among the indenoquinoline compounds, NSC 706744, NSC 725776 and NSC 724998 showed a prominent antitumor activities in vitro and in vivo, and Top1 inhibitory activities, of which the latter two have entered the NCI's clinical research.

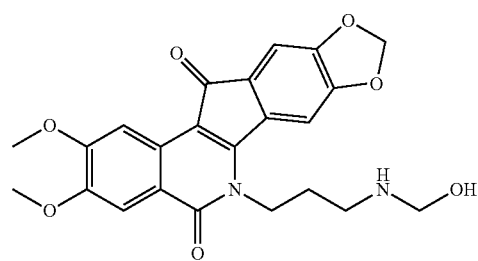

NSC 706744

-continued

NSC725776

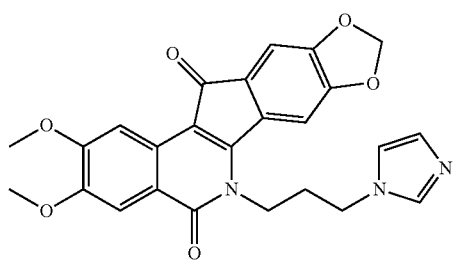

NSC724998

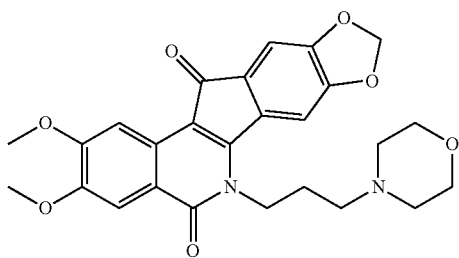

Comparing with camptothecins, indenoisoquinolines have several unique advantages: 1) the chemical structures of such compounds are very stable, while camptothecin molecule contains hydroxy lactone ring which is readily hydrolyzed; 2) NSC 314622 can cause Top1 mediated DNA cleavage, but the resulted cleavage sites are different from CPT, which may contribute to target different action sites on the genome, therefore, it is likely to find effective anti-tumor medicaments having treatment spectra different from camptothecins; 3) a ternary complex formed from these compounds with the Top1-DNA complex is more stable. The cleavage complex formed from camptothecins is reversible, therefore it is necessary to takes a long time for intravenous dripping to better exert anti-tumor activity. The advantage of these compounds can overcome this problem; 4) these compounds help to overcome the shortcomings of camptothecins such as resistance, poor water-solubility, and so on.

The research experience of the topoisomerase II and tubulin inhibitors has showed that the anticancer drugs having same mechanism of action but different skeletons could have different anti-tumor spectra. Therefore, it is urgent to develop novel non-camptothecin Top1 inhibitors with new skeletons, high efficiencies and low toxicities.

SUMMARY OF THE INVENTION

The subject of the present invention is to provide a novel indenoquinolone compound or the pharmaceutically acceptable salts thereof. The present invention also discloses the preparation, medical use and composition of the compound.

Based on the indenoisoquinolone Top1 inhibitors which have currently entered the NCI clinical studies, scaffold hopping technology and computer-aided drug design technology were used and a series of novel indenoquinolone Top1 inhibitors were designed and synthesized in the present invention. The activity tests against a variety of tumor cells indicated that these compounds have good broad-spectra anti-tumor activities, especially exhibited significant anti-tumor activities against a variety of solid tumors such as the liver cancer, etc., therefore, these compounds are expected to be developed as novel promising anti-tumor medicaments.

In the first aspect of the invention, an indenoquinolone compound of the general formula (A), or the pharmaceutically acceptable salt, solvate, prodrug or polymorph thereof is provided:

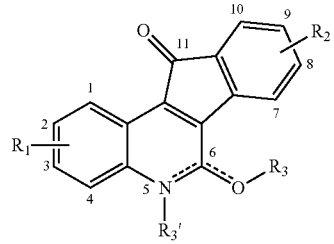

(A)

wherein, $R_1$ may be located at position 1-4 and mono-, di- or multi-substituted; $R_2$ may be located at position 7-10 and mono-, di- or multi-substituted; wherein $R_1$ or $R_2$ is any one of the following groups: a) a hydrogen; b) a substituted or unsubstituted C1-8 straight-chain or branched alkyloxy; c) a substituted or unsubstituted C1-8 straight-chain or branched alkyl; d) a substituted or unsubstituted C2-6 straight-chain or branched alkenyl; e) a substituted or unsubstituted C2-6 straight-chain or branched alkynyl; f) a substituted or unsubstituted C1-8 straight-chain or branched alkyl amide group; g) a substituted or unsubstituted aryl group or a 5-6 membered heterocyclic aryl; h) a substituted or unsubstituted C1-8 straight-chain or branched alkanoyl; i) a substituted or unsubstituted C1-8 straight-chain or branched alkanoyloxy; j) a nitro; k) an amino; l) a hydroxy; m) a halogen; n) a methylenedioxy; o) an ethylenedioxy; p) a cyano;

one of $R_3$ and $R_3'$ is absent, and the other is —$(CH_2)_mR_4$, wherein m is 1-8, $R_4$ can be a saturated or unsaturated nitrogen-containing heterocycle, halogen, or $NR_5R_6$, wherein $R_5$ or $R_6$ is any one of the following groups: a) a hydrogen; b) a substituted or unsubstituted C1-8 straight-chain or branched alkyl; c) a substituted or unsubstituted aryl or a 3-8 membered heterocyclic aryl; and when $R_3$ is absent, the bond between O and C at 6-position is a double bond and the bond between N and C at 6-position is a single bond; when $R_3'$ is absent, the bond between O and C at 6-position is a single bond and the bond between N and C at 6-position is a double bond;

the "substituted" refers to being substituted by one or more of the following substituents: C1-5 alkyl, C2-5 alkenyl, C2-5 alkynyl, C1-5 alkyloxy, halogen, nitro, cyano, hydroxyl, amino, carboxyl, and oxo.

In another preferred embodiment, the compound has general formula (I) or (II):

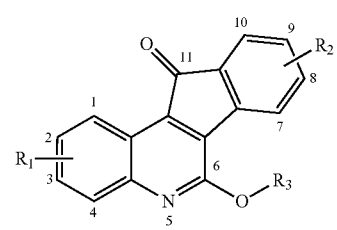

(I)

-continued

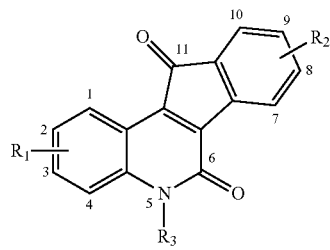
(II)

wherein, $R_1$, $R_2$ and $R_3$ are defined as above.

In another preferred embodiment, $R_1$ is mono- or di-substituted and located at 2- and 3-position.

In another preferred embodiment, $R_2$ is mono- or di-substituted and located at 8- and 9-position.

In another preferred embodiment, $R_1$ may be located at one or two positions of 2- and 3-position; and/or $R_2$ may be located at one or two positions of 8- and 9-position.

In another preferred embodiment, $R_1$ is any one of the following groups: a) a hydrogen; b) a C1-8 straight-chain or branched alkyloxy; c) a halogen; and/or $R_2$ is any one of the following groups: a) a hydrogen; b) a C1-8 straight-chain or branched alkyloxy; c) a halogen; and/or $R_3$ is —$(CH_2)mR_4$, wherein m is 1-4, and $R_4$ may be a saturated or unsaturated 4-7 membered nitrogen-containing heterocycle, halogen, or $NR_5R_6$, wherein $R_5$, or $R_6$ is any one of the following groups: a) a hydrogen; b) a substituted or unsubstituted C1-8 straight-chain or branched alkyl.

In another preferred embodiment, m is 2-5, more preferably, is 2-3.

In another preferred embodiment, m in $R_3$ is 2-3, and $R_4$ may be a saturated or unsaturated 5-6 membered nitrogen-containing heterocycle, halogen, or $NR_5R_6$, wherein $R_5$ or $R_6$ is any one of the following groups: a) a hydrogen; b) a substituted or unsubstituted C1-8 straight-chain or branched alkyl.

In another preferred embodiment, when $R_1$ is mono-substituted, $R_1$ is located at 2-position, and is C1-8 straight-chain or branched alkoxy; and when $R_1$ is di-substituted, $R_1$ is located at 2- and 3-position, and is C1-8 straight-chain or branched alkoxy.

In another preferred embodiment, $R_2$ is located at 9-position, and $R_2$ is hydrogen, halogen or C1-8 straight-chain or branched alkoxy.

In another preferred embodiment, $R_3$ is halo-ethyl, dimethylamino-ethyl, diethylamino-ethyl, piperidyl-ethyl, morpholinyl-ethyl, pyrrolidinyl-ethyl, imidazolyl-ethyl, dimethylamino-propyl, diethylamino-propyl, piperidyl-propyl, morpholinyl-propyl, pyrrolidinyl-propyl, imidazolyl-propyl.

In another preferred embodiment, $R_3$ is —$CH_2CH_2Br$.

In another preferred embodiment, the compound is compounds 1-50, more preferably, is compounds 1, 6, 12, 14, 15, 20, 31, 44 and 46.

In the second aspect of the invention, a composition comprising the compound of the first aspect of the invention or the pharmaceutically acceptable salts thereof, and a pharmaceutically acceptable carrier is provided.

In another preferred embodiment, the composition is pharmaceutical composition.

In the third aspect of the invention, a use of the compound of the first aspect of the invention or the pharmaceutically acceptable salt thereof is provided. It can be used (a) in the preparation of antitumor, antifungal, antiviral agents; (b) in the preparation of a pharmaceutical composition for inhibiting topoisomerase I; and/or (c) as a topoisomerase I inhibitor.

In another preferred embodiment, the tumor is non-small cell lung cancer, colon cancer, breast cancer, or liver cancer.

In the fourth aspect of the invention, a preparation method for the compound of the first aspect of the invention is provided, said method comprising the following step:

reacting the compound of formula VII with $R_3X$ or the salt thereof in an inert solvent under alkaline conditions to form the compound of formula I and II,

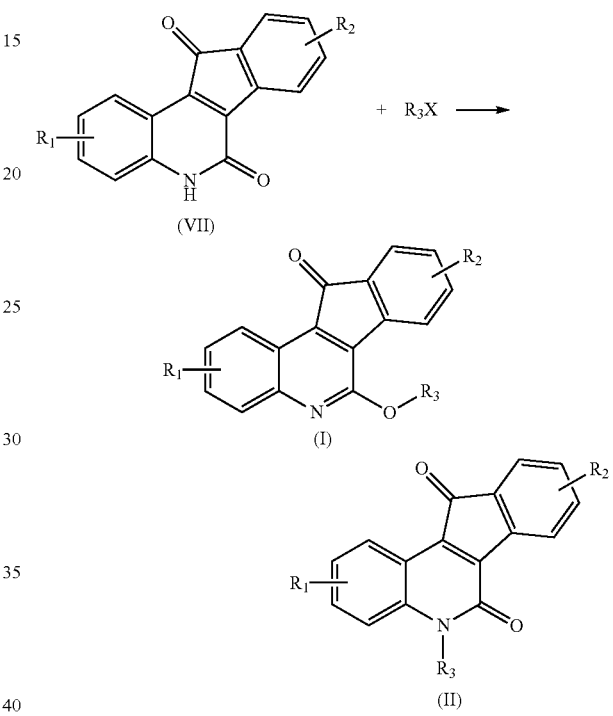

wherein, $R_1$, $R_2$, and $R_3$ are defined as above, X is a leaving group, and the salt of $R_3X$ is an inorganic acid salt or organic acid salt.

More preferably, the leaving group includes halogen or other large negatively charged group, such as benzenesulfonate group, p-toluenesulfonate group, trifluoromethanesulfonate group, and the like.

In another preferred embodiment, the reaction is carried out under alkaline conditions (e.g., in the presence of sodium carbonate, potassium carbonate, and/or sodium hydride, etc.)

In another preferred embodiment, the reaction time is 0.5-24 hours.

In another preferred embodiment, the inert solvents include: DMF, DMSO, or the combination thereof.

In another preferred embodiment, the method comprises:

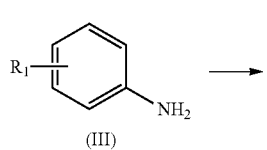
(III)

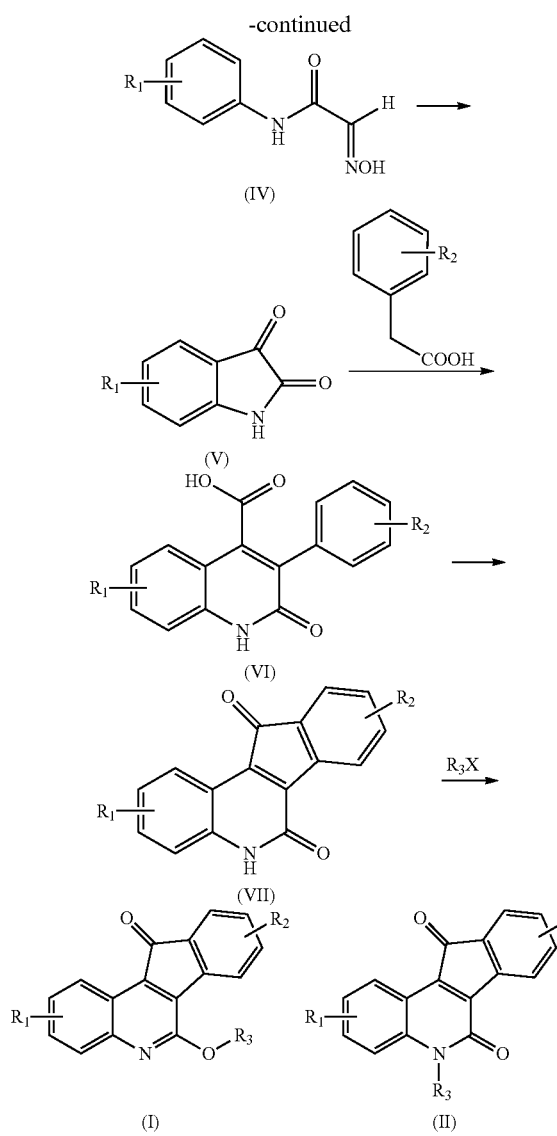

wherein, $R_1$, $R_2$, $R_3$, X and the salt of $R_3$X is described as above.

In another preferred embodiment, the inorganic acid used in the synthesis of intermediates (IV) is hydrochloric acid.

In another preferred embodiment, the organic acid used in the synthesis of intermediates (V) is concentrated sulfuric acid or methanesulfonic acid.

In another preferred embodiment, the organic sodium salt used in the synthesis of intermediates (VI) is sodium acetate.

In another preferred embodiment, the organic solvent used in the synthesis of target compound (I) or (II) is anhydrous DMF.

In the fifth aspect of the present invention, an in vitro non-therapeutic method for inhibiting topoisomerase I is provided, comprising the step of contacting topoisomerase I with the compound of the first aspect.

In the sixth aspect of the present invention, a method for inhibiting topoisomerase I is provided, comprising the step of administering the compound of the first aspect or the pharmaceutical composition of the second aspect to the subject in need thereof.

In the seventh aspect of the present invention, a treatment method for the disease associated with the topoisomerase I is provided, comprising the step of administering the compound of the first aspect or the pharmaceutical composition of the second aspect to the subject in need thereof.

In another preferred embodiment, said disease associated with the topoisomerase I includes cancer (such as non-small cell lung cancer, colon cancer, breast cancer or liver cancer).

In another preferred embodiment, said subject includes mammals (such as man).

In another preferred embodiment, the administered dose is safe and effective amount.

In the eighth aspect of the present invention, a preparation method for the pharmaceutical composition is provided, comprising the step of mixing the compound or the pharmaceutically acceptable salt thereof of the first aspect with a pharmaceutically acceptable carrier, thereby forming the pharmaceutical composition.

It should be understood that, within the scope of the present invention, the technical features specifically described above and below (such as the Examples) can be combined with each other, thereby constituting a new or preferred technical solution which needs not be described one by one.

DETAILED DESCRIPTION OF THE INVENTION

Upon extensive and in-depth research, the inventors have designed and synthesized indenoquinolone compounds with novel structure for the first time based on the representative indenoisoquinolone Top1 inhibitors as known and by using the scaffold hopping technology for converting B ring into ring lactam. The compounds of the present invention have stable chemical structures and good water solubility. The experimental results showed that the compounds have significant Top1 inhibitory activities and broad spectra of anti-tumor activity, especially for liver cancer, lung cancer, breast cancer, colon cancer and other solid tumors. Thus, the present invention has been completed.

In the present invention, the compounds of formula (I) and those of formula (II) can be regarded as isomers. In the preparation of such compounds, reactive intermediates obtained by removing the proton from the amide under alkaline environment exist in two main resonance forms, i.e. the amide anion with negative charge on N and the phenolic oxygen anion with a negative charge on O, and both of which can be reacted with an electrophilic reagent (such as halogenated hydrocarbons, sulfonic acid esters, etc.), thereby generating two alkylated objective compounds simultaneously.

According to the present invention, the aryl is an atomic group obtained by removing one hydrogen atom from the aromatic hydrocarbon molecules. The aromatic hydrocarbon is a compound having aromaticity and has stable chemical properties. The properties of the aromatic hydrocarbon are different from those of the general saturated compounds, for example, it is difficult for the addition reaction and oxidization, but readily for the substitution, and the carbocyclic ring is unusually stable. The aromatic hydrocarbon includes: 1) a monocyclic aromatic hydrocarbon with only one benzene ring in the molecule, such as benzene, toluene, ethylbenzene, styrene, etc.; 2) a polycyclic aromatic hydrocarbon with two or more benzene rings in the molecule, such as biphenyl, naphthyl, anthracene, phenanthrene, etc.; 3) non-benzene aromatic hydrocarbon, which does not contain benzene ring in the molecule, but contains aromatic hydrocarbyl, the structure and property of which are similar to those of benzene ring, and has the characteristics of the aromatic compound, such as cyclopentadienyl anion, etc.

The substituted aryl refers to a group obtained by substituting other substituent for the hydrogen atom(s) on the aryl.

In the present invention, the heterocyclic aryl, unless otherwise specified, represents a stable 5- or 6-membered monocyclic aromatic ring system, or a 9 or 10-membered benzene-fused aromatic heterocyclic ring system or bicyclic fused aromatic heterocyclic ring system, which consists of carbon atoms and 1-4 hetero-atoms selected from N, O, or S, wherein N, and S hetero-atoms can be optionally oxidated, and N hetero-atom can also be optionally quaternized.

In further preferred embodiment of the present invention, $R_1$ may be located at one or both of 2- and 3-position, and $R_1$ is any one of the following groups: a) a hydrogen; b) a substituted or unsubstituted C1-8 straight-chain or branched alkyloxy; c) a substituted or unsubstituted C1-8 straight-chain or branched alkyl; d) a substituted or unsubstituted C2-6 straight-chain or branched alkenyl; e) a substituted or unsubstituted C2-6 straight-chain or branched alkynyl; f) a substituted or unsubstituted C1-8 straight-chain or branched alkyl amide group; g) a substituted or unsubstituted aryl or a 5-6 membered heterocyclic aryl; h) a substituted or unsubstituted C1-8 straight-chain or branched alkanoyl; i) a nitro; j) an amino; k) a hydroxy; l) a halogen; m) a methylenedioxy; or n) an ethylenedioxy. $R_2$ may be located at one or both of 8- and 9-position, and $R_2$ is any one of the following groups: a) a hydrogen; b) a substituted or unsubstituted C1-8 straight-chain or branched alkyloxy; c) a substituted or unsubstituted C1-8 straight-chain or branched alkyl; d) a substituted or unsubstituted C2-6 straight-chain or branched alkenyl; e) a substituted or unsubstituted C2-6 straight-chain or branched alkynyl; f) a substituted or unsubstituted C1-8 straight-chain or branched alkyl amide group; g) a substituted or unsubstituted aryl or a 5-6 membered heterocyclic aryl; h) a substituted or unsubstituted C1-8 straight-chain or branched alkanoyl; i) a nitro; j) an amino; k) a hydroxy; l) a halogen; m) a methylenedioxy; n) an ethylenedioxy. $R_3$ is —$(CH_2)_m R_4$, wherein m is 1-8, $R_4$ can be a saturated or unsaturated nitrogen-containing heterocycle, halogen, or $NR_5R_6$, wherein $R_5$ or $R_6$ is any one of the following groups: a) a hydrogen; b) a substituted or unsubstituted C1-8 straight-chain and branched alkyl; c) a substituted or unsubstituted aryl or a 5-6 membered heterocyclic aryl. The "substituted" refers to being substituted by one or more of the following substituents: C1-5 alkyl, C2-5 alkenyl, C2-5 alkynyl, C1-5 alkyloxy, halogen, nitro, cyano, hydroxyl, amino, carboxyl, and oxo.

In a preferred embodiment of the present invention, $R_1$ may be located at one or both of 2- and 3-position, and $R_1$ is any one of the following groups: a) a hydrogen; and b) a C1-8 straight-chain or branched alkyloxy. $R_2$ may be located at one or both of 8- and 9-position, and $R_2$ is any one of the following groups: a) a hydrogen; b) a C1-8 straight-chain or branched alkyloxy; and c) a halogen. $R_3$ is —$(CH_2)_m R_4$, wherein m is 1-4, $R_4$ can be a saturated or unsaturated 4-7 membered nitrogen-containing heterocycle, halogen, or $NR_5R_6$, wherein $R_5$ or $R_6$ is any one of the following groups: a) a hydrogen; and b) a substituted or unsubstituted C1-8 straight-chain and branched alkyl.

In a preferred embodiment of the present invention, $R_1$ may be located at one or both of 2- and 3-position, and $R_1$ is any one of the following groups: a) a hydrogen; b) a C1-8 straight-chain or branched alkyloxy. $R_2$ may be located at one or both of 8- and 9-position, and $R_2$ is any one of the following groups: a) a hydrogen; b) a C1-8 straight-chain or branched alkyloxy; and c) a halogen. $R_3$ is —$(CH_2)_m R_4$, wherein m is 1-4, $R_4$ can be a saturated or unsaturated 5-6 membered nitrogen-containing heterocycle, halogen, or $NR_5R_6$, wherein $R_5$ or $R_6$ is any one of the following groups: a) a hydrogen; and b) a substituted or unsubstituted C1-8 straight-chain and branched alkyl.

More preferably, m in $R_3$ is 2-3, and $R_4$ can be a saturated or unsaturated 5-6 membered nitrogen-containing heterocycle, halogen, or $NR_5R_6$, wherein $R_5$ or $R_6$ is any one of the following groups: a) a hydrogen; and b) a substituted or unsubstituted C1-8 straight-chain and branched alkyl.

More preferably, in the indenoquinolone compounds according to the present invention, when $R_1$ is mono-substituted, $R_1$ is located at 2-position and is a C1-8 straight-chain or branched alkyl, and when $R_1$ is di-substituted, $R_1$ is located at 2- and 3-position and is a C1-8 straight-chain or branched alkyloxy.

More preferably, in the indenoquinolone compounds according to the present invention, $R_2$ is located at 9-position, and is a hydrogen, halogen or C1-8 straight-chain and branched alkyloxy.

More preferably, in the indenoquinolone compounds according to the present invention, $R_3$ is haloethyl, dimethylamino ethyl, diethylamino ethyl, piperidyl ethyl, morpholinyl ethyl, pyrrolidinyl ethyl, imidazolyl ethyl, dimethylamino propyl, diethylamino propyl, piperidyl propyl, morpholinyl propyl, pyrrolidinyl propyl, imidazolyl propyl.

In the examples of the present invention, the combination of each substituent in the indenoquinolone of formula (I) can include, but not limited to, the following table.

| Compound No. | 2-position | 3-position | 8-position | 9-position | $R_3$ |
|---|---|---|---|---|---|
| 1 | H | H | H | $OCH_3$ | $CH_2CH_2N(CH_3)_2$ |
| 2 | H | H | H | $OCH_3$ | $CH_2CH_2N(CH_2CH_3)_2$ |
| 3 | H | H | H | $OCH_3$ | $CH_2CH_2N$-pyrrolidinyl |
| 4 | H | H | H | $OCH_3$ | $CH_2CH_2N$-imidazolyl |
| 5 | H | H | H | $OCH_3$ | $CH_2CH_2N$-morpholinyl |
| 6 | H | H | H | $OCH_3$ | $CH_2CH_2CH_2N(CH_3)_2$ |
| 7 | H | H | H | Cl | $CH_2CH_2N(CH_3)_2$ |
| 8 | H | H | H | Cl | $CH_2CH_2N(CH_2CH_3)_2$ |
| 9 | H | H | H | Cl | $CH_2CH_2N$-pyrrolidinyl |
| 10 | H | H | H | Cl | $CH_2CH_2N$-imidazolyl |
| 11 | H | H | H | Cl | $CH_2CH_2N$-piperidinyl |
| 12 | H | H | H | Cl | $CH_2CH_2CH_2N(CH_3)_2$ |
| 13 | $OCH_3$ | H | H | $OCH_3$ | $CH_2CH_2N(CH_3)_2$ |
| 14 | $OCH_3$ | H | H | $OCH_3$ | $CH_2CH_2N(CH_2CH_3)_2$ |
| 15 | $OCH_3$ | H | H | $OCH_3$ | $CH_2CH_2N$-piperidinyl |
| 16 | $OCH_3$ | H | H | $OCH_3$ | $CH_2CH_2CH_2N(CH_3)_2$ |
| 17 | $OCH_3$ | H | $OCH_3$ | H | $CH_2CH_2N(CH_3)_2$ |

-continued

| Compound No. | 2-position | 3-position | 8-position | 9-position | R₃ |
|---|---|---|---|---|---|
| 18 | OCH₃ | H | H | Br | CH₂CH₂N-pyrrolidinyl |
| 19 | OCH₃ | H | H | Br | CH₂CH₂N-imidazolyl |
| 20 | OCH₃ | OCH₃ | H | OCH₃ | CH₂CH₂N(CH₃)₂ |
| 21 | OCH₃ | OCH₃ | H | OCH₃ | CH₂CH₂N(CH₂CH₃)₂ |
| 22 | OCH₃ | OCH₃ | H | OCH₃ | CH₂CH₂N-pyrrolidinyl |
| 23 | OCH₃ | OCH₃ | H | OCH₃ | CH₂CH₂N-morpholinyl |
| 24 | OCH₃ | OCH₃ | H | OCH₃ | CH₂CH₂N-piperidinyl |
| 25 | OCH₃ | OCH₃ | H | OCH₃ | CH₂CH₂CH₂N(CH₃)₂ |
| 26 | OCH₃ | OCH₃ | H | Cl | CH₂CH₂N(CH₃)₂ |
| 27 | OCH₃ | OCH₃ | H | Cl | CH₂CH₂N-imidazolyl |
| 28 | OCH₃ | OCH₃ | H | Cl | CH₂CH₂N-morpholinyl |
| 29 | OCH₃ | OCH₃ | H | Cl | CH₂CH₂CH₂N(CH₃)₂ |
| 30 | H | H | H | OCH₃ | CH₂CH₂Br |

In the examples of the present invention, the combination of each substituent in the indenoquinolone of formula (H) can include, but not limited to, the following table.

| Compound No. | 2-position | 3-position | 8-position | 9-position | R₃ |
|---|---|---|---|---|---|
| 31 | H | H | H | OCH₃ | CH₂CH₂N(CH₃)₂ |
| 32 | H | H | H | OCH₃ | CH₂CH₂N-pyrrolidinyl |
| 33 | H | H | H | OCH₃ | CH₂CH₂N-morpholinyl |
| 34 | H | H | H | OCH₃ | CH₂CH₂CH₂N(CH₃)₂ |
| 35 | H | H | H | Cl | CH₂CH₂N(CH₃)₂ |
| 36 | H | H | H | Cl | CH₂CH₂N(CH₂CH₃)₂ |
| 37 | H | H | H | Cl | CH₂CH₂N-pyrrolidinyl |
| 38 | H | H | H | Cl | CH₂CH₂N-imidazolyl |
| 39 | H | H | H | Cl | CH₂CH₂N-piperidinyl |
| 40 | H | H | H | Cl | CH₂CH₂CH₂N(CH₃)₂ |
| 41 | OCH₃ | H | H | OCH₃ | CH₂CH₂N(CH₃)₂ |
| 42 | OCH₃ | H | OCH₃ | H | CH₂CH₂N(CH₂CH₃)₂ |
| 43 | OCH₃ | H | H | Br | CH₂CH₂N-imidazolyl |
| 44 | OCH₃ | OCH₃ | H | OCH₃ | CH₂CH₂N-pyrrolidinyl |
| 45 | OCH₃ | OCH₃ | H | OCH₃ | CH₂CH₂N-morpholinyl |
| 46 | OCH₃ | OCH₃ | H | OCH₃ | CH₂CH₂CH₂N(CH₃)₂ |
| 47 | OCH₃ | OCH₃ | H | Cl | CH₂CH₂N(CH₃)₂ |
| 48 | OCH₃ | OCH₃ | H | Cl | CH₂CH₂N-imidazolyl |
| 49 | OCH₃ | OCH₃ | H | Cl | CH₂CH₂N-morpholinyl |
| 50 | OCH₃ | OCH₃ | H | Cl | CH₂CH₂CH₂N(CH₃)₂ |

Another purpose of the present invention is to provide the preparation method for the above-mentioned indenoquinolone compounds.

A compound of formula (A) of the present invention can be prepared by the following method. However, the conditions of this method, for example, reactants, solvents, alkali, the amount of the compound used, the reaction temperature, and the time required for the reaction etc. is not limited to the following explanation. The compounds of the present invention may also be conveniently prepared by optionally combining the method described in the present specification and a variety of synthetic methods known to those skilled in the art. Such combination may be readily carried out by the skilled in the art.

In the preparation method of the present invention, each reaction is usually performed in an inert solvent, at −20° C. to reflux temperature (preferably, from −10° C. to 100° C., more preferably from 0° C. to 80° C.). The reaction time is usually from 0.1 hours to 24 hours, preferably 0.5 to 12 hours, more preferably 1 to 5 hours.

In a preferred embodiment, the method includes the following steps:

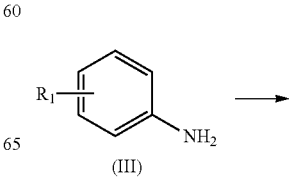

(III)

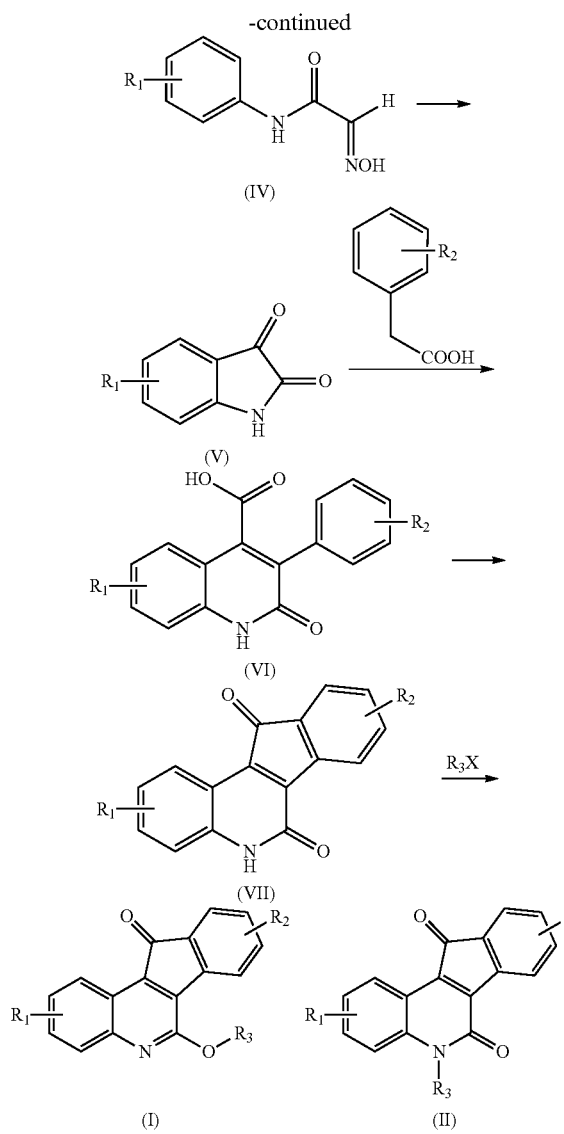

wherein $R_1$, $R_2$, and $R_3$ are defined as above, and X is a leaving group (such as a halogen or other negatively charged groups which are easily leaved, such as sulfonate group);

(1) Synthesis of Intermediate (IV) Chloral hydrate, hydroxylamine hydrochloride, and various substituted anilines (III) were added into a dilute inorganic acid and stirred. The reaction system was heated to 40-70° C. to form the intermediate (IV). Preferably, the inorganic acid used is hydrochloric acid.

(2) Synthesis of the Intermediates (V)

Intermediate (IV) was heated to 80-100° C. in an organic acid to form the intermediate (V). Preferably, the organic acid used is concentrated sulfuric acid or methanesulfonic acid.

(3) Synthesis of the Intermediates (VI)

The intermediate (V), an organic acid sodium salt and various substituted phenylacetic acid were mixed and heated to 150-200° C. to form intermediate (VI). Preferably, the organic acid sodium salt is sodium acetate.

(4) General Method for the Synthesis of Intermediate (VII)

The intermediate (VI) was added to polyphosphoric acid (PPA), and heated to 80-130° C. to give the intermediate (VII).

(5) General Method for the Synthesis of the Object Compound (I) or (II)

The intermediate (VII) was dissolved in an organic solvent. An alkali was added with stirring. A variety of halogenated hydrocarbons or the salts thereof were added with heating and stirring to obtain the objective compound (I) or (II). Preferably, the organic solvent used is anhydrous DMF.

Said salts of halogenated hydrocarbon include inorganic acid salts (e.g. hydrochloride, sulfate, phosphate, etc.) and organic acid salts (such as acetate, methanesulfonate, malate, etc.).

More specifically, the preparation of indenoquinolone compounds according to the present invention comprises the following steps:

(1) A variety of anilines substituted at benzene ring (III), chloral hydrate, hydroxylamine hydrochloride, and anhydrous sodium sulfate were heated to 40-100 V in an aqueous solvent to obtain hydroxyimino acetanilides substituted at benzene ring (IV);

(2) A variety of hydroxyimino acetanilides substituted at benzene ring (IV) were heated in methyl sulfonic acid to obtain isatins substituted at benzene ring (V);

(3) A variety of isatins substituted at benzene ring (V) and various substituted phenylacetic acid were heated to 150-200 V with sodium acetate as catalyst, to form the intermediates substituted at benzene ring (VI);

(4) A variety of intermediates substituted at benzene ring (VI) were heated to 80 to 130 V in polyphosphoric acid to form various intermediates substituted at benzene ring (VII);

(5) In the presence of sodium hydride, a variety of intermediates substituted at benzene ring (VII) reacted in DMF with various chlorinated hydrocarbons or the salts thereof to form the compounds of formula (I) or (II) substituted at benzene ring.

Some indenoquinolone compounds of the present invention can be prepared into their pharmaceutically acceptable salts or other common prodrugs (which can be converted into active forms in vivo when administered in prodrug form) by conventional methods. The salts include inorganic acid salts and organic acid salts, wherein, inorganic acids include (but not limited to) hydrochloric acid, sulfuric acid, phosphoric acid, diphosphoric acid, hydrobromic acid, nitric acid, etc.; organic acids include (but not limited to) acetic acid, maleic acid, fumaric acid, tartaric acid, succinic acid, lactic acid, methanesulfonic acid, p-toluenesulfonic acid, salicylic acid, oxalic acid, etc. Furthermore, the compounds of the present invention also include other common prodrugs (which can be converted into active forms in vivo when administered in the prodrug form).

The compounds of the formula (A) of the present invention have Top1 inhibiting effects and anti-tumor activities. Protein sequences of Top1 superfamily are conservative, and the prior arts also suggest that the compounds of the present invention have antiviral activity (Journal of Biological Chemistry, 1994, 269:7051) and antifungal activity (FEMS Microbiology Letters, 1996, 138:105), therefore the compounds of the present invention can be used to prepare the corresponding therapeutic drugs.

The compounds of the present invention have good anti-tumor activities. They can be used to treat tumors, including but not limited to, the tumors occur in esophagus, stomach, intestines, rectum, mouth, pharynx, larynx, lung, colon, breast, uterus, endometriuml, ovary, prostate, testicle, bladder, kidney, liver, pancreas, bone, connective tissue, skin, eye, brain and central nervous system, etc. as well as thyroid cancer, leukemia, Hodgkin's disease, lymphoma, myeloma and the like.

Pharmaceutical Composition and Administration Method

Due to pharmacological activities of indenoquinolone compounds of the present invention, they can be used for preparing anti-tumor, anti-fungal and antiviral medicaments. Therefore, the invention also includes pharmaceutical compositions with these compounds or the pharmaceutically acceptable salts thereof as active ingredients. The pharmaceutical composition further comprises a pharmaceutically acceptable carrier, which can be in solid form or liquid form. The dosage form may be tablet, capsule, powder, granule, suspension, or injection.

The present invention also includes a therapeutic method which comprises administering a pharmaceutically effective amount of the compounds of the formula (A) or the pharmaceutically acceptable salt thereof to a mammal.

When the compounds of the present invention were used for the above purposes, they can be mixed with one or more pharmaceutically acceptable carriers or excipients, such as solvent, and diluent, etc., and can be administered orally with the following forms: tablet, pill, capsule, dispersible powder, granule, or suspension (containing, e.g. about 0.05-5% suspending agent), syrup (containing, e.g. about 10-50% sugar), and elixir (containing about 20-50% ethanol), or externally with the following forms: ointment, gel, medicated tape, etc., or parenterally using a sterile injectable solution or suspension (containing about 0.05-5% suspending agent in an isotonic medium). For example, these pharmaceutical preparations may contain about 0.01-99%, more preferably about 0.1%-90% (by weight) of the active ingredient mixed with a carrier.

The effective dose of the active ingredient used can be varied with the compounds used, the mode of administration and the severity degree of the disease to be treated. However, satisfactory results can be obtained, when the compounds of the present invention were administered with the daily dose of about 0.25-1000 mg/kg animal weight; preferably, administered with 2-4 divided doses everyday, or administered in the form of sustained release. For most of the large mammals, the total daily dose is about 1-100 mg/kg, preferably about 2-80 mg/kg. Dosage forms suitable for oral administration contain about 0.25-500 mg of the active compounds intimately mixed with a solid or liquid pharmaceutically acceptable carrier. The dose can be adjusted to provide the optimal therapeutic response. For example, according to the urgent requirements of the treatment status, several divided doses can be administered daily or the dose can be reduced proportionally.

These active compounds may be administered through the oral, intratumor, intravenous, intramuscular or subcutaneous route, etc. The solid carriers include: starch, lactose, dicalcium phosphate, microcrystalline cellulose, sucrose and kaolin, while liquid carriers include: sterile water, polyethylene glycol, nonionic surfactant and edible oil (such as corn oil, peanut oil and sesame oil), as long as the carriers are suitable for the properties of the active ingredient and the particular administration mode as desired. Adjuvants normally used in the preparation of pharmaceutical compositions may also advantageously be included, such as flavoring agents, pigments, preservatives and antioxidants such as vitamin E, vitamin C, BHT and BHA.

For being prepared and administrated readily, the preferred pharmaceutical composition is a solid composition, particularly tablets and solid filled or liquid filled capsules. Preferably, compounds are administered through intratumoral and oral routes.

These active compounds may also be administrated parenterally or intraperitoneally. The solution or suspension of these active compounds (as free base or pharmaceutically acceptable salt) can be prepared in water properly containing surfactant (such as hydroxypropyl cellulose, polyvinyl pyrrolidone). Further, the dispersion can be prepared in glycerol, liquid, polyethylene glycols and mixtures thereof in the oil. Under the conditions of conventional storage and use, these preparations can contain a preservative to prevent the growth of microorganisms.

The drug forms suitable for the injection include: a sterile aqueous solution or dispersion and sterile powder (for the extemporaneous preparation of sterile injectable solution or dispersion). In all cases, the forms must be sterile and fluid for being discharged from a syringe. Further, the forms must be stable under the conditions of manufacture and storage, and the pollution of the microorganisms (such as bacteria and fungi) should be prevented. The carrier can be a solvent or dispersion medium containing water, alcohol (such as glycerol, propylene glycol and liquid polyethylene glycol), appropriate mixtures thereof, and vegetable oils.

In addition, the compounds of the present invention also can be combined with one (or more) other anticancer active ingredient, especially anticancer compound, for example an alkylating agent, such as an alkyl sulfonate (busulfan), dacarbazine, procarbazine, nitrogen mustard compounds (chlormethine, phenylalanine mustard, leukeran), cyclophosphamide or ifosfamide; nitrosoureas, such as carmustine, lomustine, semustine or streptozocin; antitumor alkaloids, such as vincristine or vinblastine; taxane, such as Taxol or Taxotere (taxotere); antitumor antibiotics, such as actinomycin; intercalative agent, antitumor metabolites, folic acid antagonists or methotrexate; purine synthesis inhibitor; purine analogs, such as 6-thioguanine; pyrimidine synthesis inhibitors, aromatase inhibitors, capecitabine or pyrimidine analogs, such as fluorouracil, gemcitabine, cytarabine and cytosine arabinoside; brequinar (brequinar), topoisomerase inhibitors, such as camptothecin or etoposide; anticancer hormone agonists and antagonists including tamoxifen; kinase inhibitor, mesylate imatinib (imatinib), growth factor inhibitors, anticancer metal complexes, anthracycline antibiotics, anti-angiogenic medicaments and the like.

The term "safe and effective dosage" refers to the amount of the compounds which is sufficient to improve the patient's condition without producing any serious side effect. The safe and effective amount was determined according to the subject's age, conditions, course of treatment, etc.

"Pharmaceutically acceptable carrier" means one or more compatible solid or liquid fillers or gel materials, which are suitable for human, and must have sufficient purity and sufficiently low toxicity. "Compatibility" herein means that the components of the composition can be blended with the compounds of the invention or with each other, and would not significantly reduce the efficacy of the compounds. Some examples of pharmaceutically acceptable carriers include sugar (such as glucose, sucrose, lactose, etc.), starch (such as corn starch, potato starch, etc.), cellulose and the derivatives thereof (such as sodium carboxymethyl cellulose, sodium ethyl cellulose, cellulose acetate, etc.), gelatin, talc, solid lubricants (such as sodium stearate, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween), wetting agent (such as sodium dodecyl sulfate), coloring agents, flavoring agents, stabilizers, antioxidants, preservatives, pyrogen-free water, etc.

The main advantages of the present invention include:

(a) A series of compounds with novel structure and strong Top1 inhibitory activities are provided.

(b) The compounds have broad-spectra anti-tumor activities and can significantly inhibit the growth of a variety of solid tumors.

(c) The compounds have good water-solubilities and stable chemical structures, so that they are expected to be developed as novel anticancer drugs.

DESCRIPTION OF THE PREFERRED EMBODIMENTS

The present invention will be further illustrated below with reference to specific examples. It should be understood that these examples are only to illustrate the present invention but not to limit the scope of the present invention. The experimental methods with no specific conditions described in the following examples are generally performed under conventional conditions or according to the manufacture's instruction. Unless indicated otherwise, the percentages, or parts are calculated by weight.

Example 1

Synthesis of 6-(2-(dimethylamino-ethoxy)-9-methoxy-11H-indeno[1,2-c]quinolin-11-one (Compound 1 in Table 1)

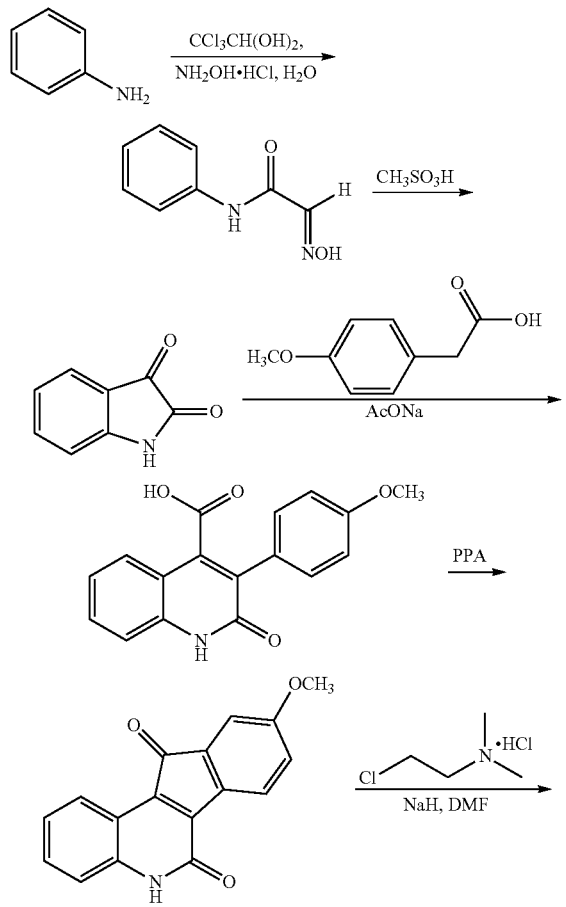

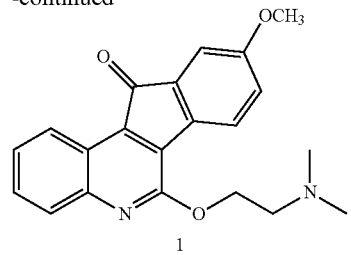

1. Synthesis of Oximino Acetanilide 25 mL $H_2O$ was added to chloral hydrate (1.49 g, 9 mmol) and anhydrous sodium sulfate (7.62 g, 54 mmol), and the mixture was rapidly stirred until clear. Hydroxylamine hydrochloride (6.84 g, 42 mmol) was added into dilute hydrochloric acid (9 mL $H_2O$: 1 mL concentrated HCl), and then, aniline (1.23 g, 8 mmol) was added. The mixture was stirred to form a suspension. The suspension was added into an aqueous solution of chloral hydrate. After stirring for 5 min, the mixture was transferred to an oil bath at 45° C. and heated for 2 h. The reaction was finished by TLC detection, and the reaction system was stirred and cooled in an ice bath, filtered and dried, to obtain a solid oximino acetanilide.

2. Synthesis of Isatin 5 mL methanesulfonic acid was heated to 50° C. and slowly added to oximino acetanilide in batches, with the temperature being maintained at 60-70° C. After feeding, the temperature was raised to 70-80° C., and the reaction was carried out for 15 min. The reaction was finished by TLC detection. The reaction solution was poured into a crushed ice, and a red solid was precipitated. After placing at low temperature (0° C.) for 10 min, the red solid was filtered and dried to give crude isatin.

Further purification: 25 g crude isatin was added into 125 mL hot water. 11 g sodium hydroxide was dissolved in 25 mL water to form a solution. The solution was added into the hot water and the solute was dissolved by stirring. 1 M dilute hydrochloric acid solution was slowly added dropwise to the aqueous solution of isatin while stirring until a small amount of solid was precipitated. After filtered, the mother liquor was acidated to pH 2-3 by adding concentrated hydrochloric acid. The mother liquor was cooled rapidly and filtered to give pure isatin.

3. Synthesis of 3-(4-methoxyphenyl)-2-oxo-1,2-dihydroquinolin-4-carboxylic acid 7.5 mmol of isatin (III), 1.875 mmol of sodium acetate, and 13.125 mmol p-methoxyphenylacetic acid were mixed, heated to 150-200° C. and refluxed for 1-5 h. The reaction was finished by TLC detection. The reaction solution was washed with petroleum ether and acetone successively. After separated by column chromatography, the title compound was obtained.

4. Synthesis of 9-methoxy-5H-indeno[1,2-c]quinoline-6,11-dione 12.3 mmol 3-(4-methoxyphenyl)-2-oxo-1,2-dihydroquinolin-4-carboxylic acid was added into 27 g of polyphosphoric acid and heated to 130° C. for 1 h. The reaction was finished by TLC detection. The reaction system was poured into ice-water, and allowed to stand. After filtered, washed with methanol and dried, the title compound was obtained. Mp: 294-296° C.; $^1$H NMR (300 MHz, DMSO-d6) δ 3.81 (s, 3H, OCH$_3$), 6.79 (s, 1H, Ar—H), 6.90-7.12 (m, 3H, Ar—H), 7.35-7.39 (m, 2H, Ar—H), 7.42 (d, 1H, J=8.1 Hz, Ar—H), 12.31-12.32 (br, 1H, NH); ESI-MS m/z (rel intensity) 278.2 [MH+, 100].

5. Synthesis of 6-(dimethylaminoethyl)-9-methoxy-11H-indeno[1,2-c]quinolin-11-one (Compound 1 in Table 1)

1 mmol 9-methoxy-5H-indeno[1,2-c]quinoline-6,11-dione was dissolved in 15 mL DMF and cooled to 0° C. 6 mmol NaH (containing 40% mineral oil) was slowly added in batches. After the addition, the ice bath was removed, and 1.2 mmol of dimethylamino-chloroethane hydrochloride was added. The reaction system was stirred for 1 h at room temperature and then placed into the oil bath pre-heated to 40-80° C. for 1-8 h. The reaction was finished by TLC detection. The solvent was removed by reduced pressure distillation. The pure compound 1 was obtained by column chromatography (Rf=0.059, petroleum ether: acetone=3:1).

Examples 2-30

Example 1 was repeated, except that different raw materials were used, thereby obtaining compounds 2-30, as follows:
(1) 9-methoxy-5H-indeno[1,2-c]quinoline-6,11-dione reacted with diethylamino chloroethane hydrochloride, pyrrolidinyl chloroethane hydrochloride, 1H-imidazolyl chloroethane hydrochloride, morpholinyl chloroethane hydrochloride, dimethylamino chloropropane hydrochloride, 1,2-dibromoethane, respectively, to synthesize compounds 2, 3, 4, 5, 6, and 30 in table 1.
(2) 9-chloro-5H-indeno[1,2-c]quinoline-6,11-dione reacted with dimethylamino chloroethane hydrochloride, diethylamino chloroethane hydrochloride, pyrrolidinyl chloroethane hydrochloride, 1H-imidazolyl chloroethane hydrochloride, piperidyl chloroethane hydrochloride, dimethylamino chloropropane hydrochloride, respectively, to synthesize compounds 7, 8, 9, 10, 11, and 12 in table 1.
(3) 2,9-dimethoxy-5H-indeno[1,2-c]quinoline-6,11-dione reacted with dimethylamino chloroethane hydrochloride, diethylamino chloroethane hydrochloride, piperidyl chloroethane hydrochloride, dimethylamino-chloropropane hydrochloride, respectively, to synthesize compounds 13, 14, 15, and 16 in table 1.
(4) 2,8-dimethoxy-5H-indeno[1,2-c]quinoline-6,11-dione reacted with dimethylamino chloroethane hydrochloride, to synthesize compound 17 in table 1.
(5) 2-methoxy-9-bromo-5H-indeno[1,2-c]quinoline-6,11-dione reacted with pyrrolidinyl chloroethane hydrochloride, 1H-imidazolyl chloroethane hydrochloride, respectively, to synthesize compounds 18 and 19 in table 1.
(6) 2,3,9-trimethoxy-5H-indeno[1,2-c]quinoline-6,11-dione reacted with dimethylamino chloroethane hydrochloride, diethylamino-chloroethane hydrochloride, pyrrolidinyl chloroethane hydrochloride, morpholinyl chloroethane hydrochloride, piperidyl chloroethane hydrochloride, dimethylamino chloropropane hydrochloride, respectively, to synthesize compounds 20, 21, 22, 23, 24, and 25 in table 1.
(7) 2,3-dimethoxy-9-chloro-5H-indeno[1,2-c]quinoline-6,11-dione reacted with dimethylamino chloroethane hydrochloride, 1H-imidazolyl chloroethane hydrochloride, morpholinyl chloroethane hydrochloride, dimethylamino chloropropane hydrochloride, respectively, to synthesize compounds 26, 27, 28, and 29 in table 1.

Example 31

Synthesis of 5-(dimethylaminoethyl)-9-methoxy-5H-indeno[1,2-c]quinoline-6,11-one (Compound 31 in Table 3)

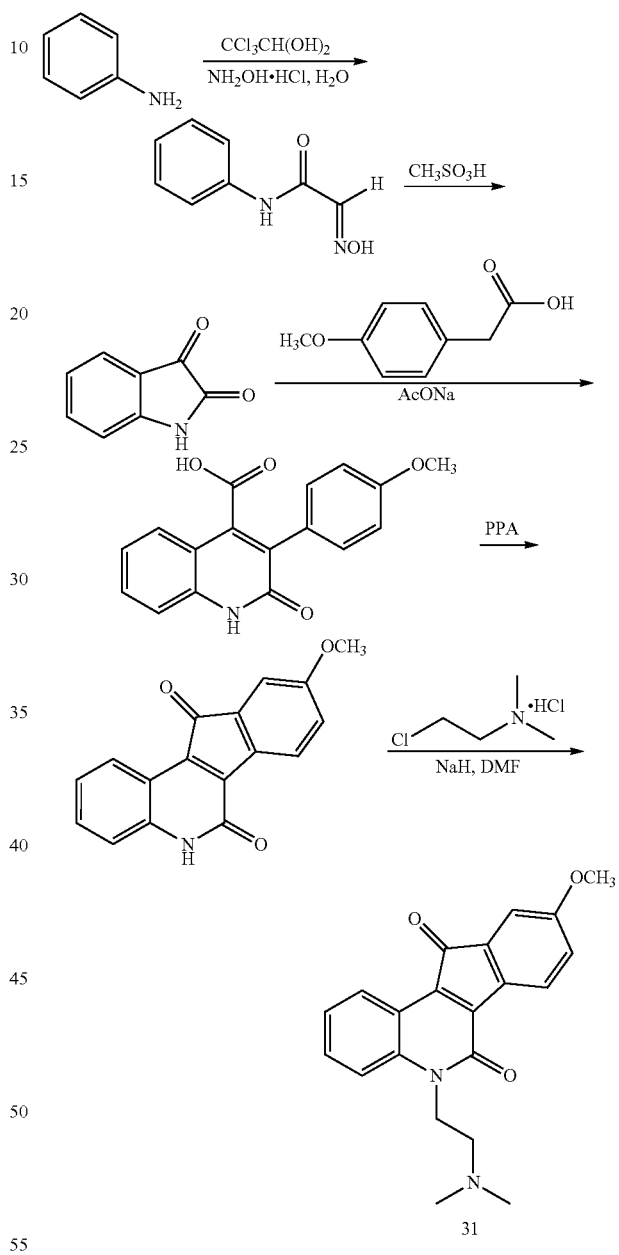

Steps 1-4 were same as Example 1.

Step 5. Synthesis of 5-(2-dimethylaminoethyl)-9-methoxy-5H-indeno[1,2-c]quinoline-6,11-dione (Compound 31 in Table 3)

1 mmol 9-methoxy-5H-indeno[1,2-c]quinoline-6,11-dione was dissolved in 15 mL DMF and cooled to 0° C. 6 mmol NaH (containing 40% mineral oil) was slowly added in batches. After the addition, the ice bath was removed, and 1.2 mmol of dimethylamino-chloroethane hydrochloride was added. After stirring for 1 h at room temperature, the reaction system was transferred into an oil bath pre-heated to 40-80° C. for 1-8 h. The reaction was finished by TLC detection. The solvent was removed by reduced pressure distillation. Then pure compound 31 was obtained by column chromatography (Rf=0.017, petroleum ether: acetone=3:1).

Compound 1 and compound 31 are two target compounds synthesized from the same reaction and can be separated and purified by column chromatography.

Examples 32-50

Example 31 was repeated, except that different materials were used to obtain compounds 32-50 as follows:

(1) 9-methoxy-5H-indeno[1,2-c]quinoline-6,11-dione reacted with pyrrolidinyl chloroethane hydrochloride, morpholinyl chloroethane hydrochloride, dimethylamino chloropropane hydrochloride, respectively, to synthesize compounds 32, 33, and 34 in Table 3.

(2) 9-chloro-5H-indeno[1,2-c]quinoline-6,11-dione reacted with dimethylamino chloroethane hydrochloride, diethylamino chloroethane hydrochloride, 1H-imidazolyl chloroethane hydrochloride, piperidyl chloroethane hydrochloride, dimethylamino chloropropane hydrochloride, respectively, to synthesize compounds 35, 36, 37, 38, 39, and 40 in table 3.

(3) 2,9-dimethoxy-5H-indeno[1,2-c]quinoline-6,11-dione reacted with dimethylamino chloroethane hydrochloride to synthesize compound 41 in Table 3.

(4) 2,8-dimethoxy-5H-indeno[1,2-c]quinoline-6,11-dione reacted with dimethylamino chloroethane hydrochloride to synthesize compound 42 in Table 3.

(5) 2-methoxy-9-bromo-5H-indeno[1,2-c]quinoline-6,11-dione reacted with 1H-imidazolyl chloroethane hydrochloride to synthesize compound 43 in Table 3.

(6) 2,3,9-trimethoxy-5H-indeno[1,2-c]quinoline-6,11-dione reacted with pyrrolidinyl chloroethane hydrochloride, morpholine chloroethane hydrochloride, dimethylamino chloropropane hydrochloride, respectively, to synthesize compounds 44, 45, and 46 in table 3.

(7) 2,3-dimethoxy-9-chloro-5H-indeno[1,2-c]quinoline-6,11-dione reacted with dimethylamino chloroethane hydrochloride, 1H-imidazolyl chloroethane hydrochloride, morpholinyl chloroethane hydrochloride, dimethylamino chloropropane hydrochloride, respectively, to synthesize compounds 47, 48, 49, and 50 in table 3.

The chemical structures of the target products of formula (I) synthesized in the present invention are shown in Table 1. The chemical structures of the target products were systematically characterized by $^1$H NMR, MS, IR and melting point. The specific data are shown in Table 1 and 2.

TABLE 1

The structures of the target compounds of formula (Ia)

(Ia)

| Compound No. | $R_{1a}$ | $R_{1b}$ | $R_{2a}$ | $R_{2b}$ | $R_3$ | melting point/° C. | MS (m/z) |
|---|---|---|---|---|---|---|---|
| 1 | H | H | OCH$_3$ | H | CH$_2$CH$_2$N(CH$_3$)$_2$ | 116-118 | 349.81 [M + H]$^+$ |
| 2 | H | H | OCH$_3$ | H | CH$_2$CH$_2$N(CH$_2$CH$_3$)$_2$ | 82-84 | 377.59 [M + H]$^+$ |
| 3 | H | H | OCH$_3$ | H | CH$_2$CH$_2$N(pyrrolidinyl) | 156-158 | 374.75 [M + H]$^+$ |
| 4 | H | H | OCH$_3$ | H | CH$_2$CH$_2$N(imidazolyl) | 177-179 | 372.33 [M + H]$^+$ |
| 5 | H | H | OCH$_3$ | H | CH$_2$CH$_2$N(morpholinyl) | 168-170 | 391.94 [M + H]$^+$ |
| 6 | H | H | OCH$_3$ | H | CH$_2$CH$_2$CH$_2$N(CH$_3$)$_2$ | 112-114 | 363.74 [M + H]$^+$ |
| 7 | H | H | Cl | H | CH$_2$CH$_2$N(CH$_3$)$_2$ | 128-130 | 353.33 [M + H]$^+$ |
| 8 | H | H | Cl | H | CH$_2$CH$_2$N(CH$_2$CH$_3$)$_2$ | 126-128 | 382.63 [M + H]$^+$ |
| 9 | H | H | Cl | H | CH$_2$CH$_2$N(pyrrolidinyl) | 136-138 | 379.67 [M + H]$^+$ |
| 10 | H | H | Cl | H | CH$_2$CH$_2$N(imidazolyl) | 193-195 | 376.57 [M + H]$^+$ |

TABLE 1-continued

The structures of the target compounds of formula (Ia)

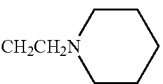

(Ia)

| Compound No. | $R_{1a}$ | $R_{1b}$ | $R_{2a}$ | $R_{2b}$ | $R_3$ | melting point/° C. | MS (m/z) |
|---|---|---|---|---|---|---|---|
| 11 | H | H | Cl | H |  | 126-128 | 393.36 [M + H]$^+$ |
| 12 | H | H | Cl | H | $CH_2CH_2CH_2N(CH_3)_2$ | 234 (dec) | 367.49 [M + H]$^+$ |
| 13 | $OCH_3$ | H | $OCH_3$ | H | $CH_2CH_2N(CH_3)_2$ | 133-135 | 379.61 [M + H]$^+$ |
| 14 | $OCH_3$ | H | $OCH_3$ | H | $CH_2CH_2N(CH_2CH_3)_2$ | 84-86 | 407.57 [M + H]$^+$ |
| 15 | $OCH_3$ | H | $OCH_3$ | H | 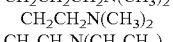 | 120-122 | 419.20 [M + H]$^+$ |
| 16 | $OCH_3$ | H | $OCH_3$ | H | $CH_2CH_2CH_2N(CH_3)_2$ | 196-198 | 393.81 [M + H]$^+$ |
| 17 | $OCH_3$ | H | H | $OCH_3$ | $CH_2CH_2N(CH_3)_2$ | 137-139 | 379.43 [M + H]$^+$ |
| 18 | $OCH_3$ | H | Br | H | 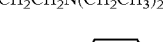 | 186-188 | 453.25 [M + H]$^+$ |
| 19 | $OCH_3$ | H | Br | H | 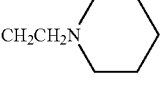 | 180-182 | 451.26 [M + H]$^+$ |
| 20 | $OCH_3$ | $OCH_3$ | $OCH_3$ | H | $CH_2CH_2N(CH_3)_2$ | 170-172 | 409.70 [M + H]$^+$ |
| 21 | $OCH_3$ | $OCH_3$ | $OCH_3$ | H | $CH_2CH_2N(CH_2CH_3)_2$ | 298 (dec) | 437.85 [M + H]$^+$ |
| 22 | $OCH_3$ | $OCH_3$ | $OCH_3$ | H | 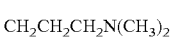 | 181-183 | 435.54 [M + H]$^+$ |
| 23 | $OCH_3$ | $OCH_3$ | $OCH_3$ | H | 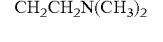 | 209-211 | 451.35 [M + H]$^+$ |
| 24 | $OCH_3$ | $OCH_3$ | $OCH_3$ | H | 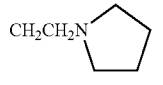 | 180-182 | 449.63 [M + H]$^+$ |
| 25 | $OCH_3$ | $OCH_3$ | $OCH_3$ | H | $CH_2CH_2CH_2N(CH_3)_2$ | 208-210 | 423.77 [M + H]$^+$ |
| 26 | $OCH_3$ | $OCH_3$ | Cl | H | $CH_2CH_2N(CH_3)_2$ | 143-144 | 413.35 [M + H]$^+$ |
| 27 | $OCH_3$ | $OCH_3$ | Cl | H | 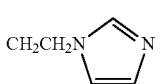 | 203-205 | 437.85 [M + H]$^+$ |
| 28 | $OCH_3$ | $OCH_3$ | Cl | H | 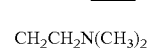 | 206-208 | 456.75 [M + H]$^+$ |
| 29 | $OCH_3$ | $OCH_3$ | Cl | H | $CH_2CH_2CH_2N(CH_3)_2$ | 260 (dec) | 427.60 [M + H]$^+$ |
| 30 | H | H | $OCH_3$ | H | $CH_2CH_2Br$ | NT | 384.92 [M + H]$^+$ |

NT = not tested; dec = decomposition

Compounds 1-30 were prepared in Examples 1-30, respectively.

TABLE 2

The $^1$H-NMR spectra and mass spectra data of the target compounds of formula (Ia)

| Compound No. | $^1$H NMR (300 MHz) | IR $\nu_{max}$ cm$^{-1}$ |
|---|---|---|
| 1 | 2.43 (s, 6H, N(CH$_3$)$_2$), 2.92 (t, 2H, CH$_2$), 3.87 (s, 3H, OCH$_3$), 4.76 (t, 2H, CH$_2$), 6.93 (dd, 1H, J$_1$ = 8.1 Hz, J$_2$ = 2.4 Hz, Ar—H), 7.19 (dd, 1H, J$_1$ = 7.2 Hz, J$_2$ = 2.4 Hz, Ar—H), 7.44 (ddd, 1H, J$_1$ = 8.1 Hz, J$_2$ = 6.9 Hz, J$_3$ = 2.4 Hz, Ar—H), 7.57 (ddd, 1H, J$_1$ = 8.1 Hz, J$_2$ = 6.9 Hz, J$_3$ = 2.4 Hz, Ar—H), 7.69 (d, 1H, J = 8.1 Hz, Ar—H), 7.80 (d, 1H, J = 8.1 Hz, Ar—H), 8.65 (dd, 1H, J$_1$ = 8.4 Hz, J$_2$ = 1.5 Hz, Ar—H); (CDCl$_3$) | 2921, 1720, 1476, 1433, 1363, 1270, 1222, 1044 |
| 2 | 1.26 (s, 6H, N(CH$_3$)$_2$), 2.76 (q, 4H, CH$_2$), 3.08 (t, 4H, CH$_2$), 3.87 (s, 3H, OCH$_3$), 4.75 (t, 2H, CH$_2$), 6.92 (dd, 1H, J$_1$ = 8.1 Hz, J$_2$ = 2.4 Hz, Ar—H), 7.19 (d, 1H, J = 2.4 Hz, Ar—H), 7.44 (ddd, 1H, J$_1$ = 8.4 Hz, J$_2$ = 6.9 Hz, J$_3$ = 1.2 Hz, Ar—H), 7.56 (ddd, 1H, J$_1$ = 8.4 Hz, J$_2$ = 6.9 Hz, J$_3$ = 1.5 Hz, Ar—H), 7.69 (d, 1H, J = 8.1 Hz, Ar—H), 7.77-7.79 (m, 1H, Ar—H), 8.64 (dd, 1H, J$_1$ = 8.4 Hz, J$_2$ = 1.5 Hz, Ar—H); (CDCl$_3$) | 2966, 2922, 1709, 1475, 1435, 1377, 1271, 1223, 1056 |
| 3 | 1.84-1.89 (m, 4H, CH$_2$), 2.74-2.79 (m, 4H, CH$_2$), 3.11 (t, 2H, CH$_2$), 3.88 (s, 3H, OCH$_3$), 4.81 (t, 2H, CH$_2$), 6.91-6.95 (m, 1H, Ar—H), 7.20 (t, 1H, Ar—H), 7.42-7.47 (m, 1H, Ar—H), 7.55-7.60 (m, 1H, Ar—H), 7.69 (dd, 1H, J$_1$ = 8.1 Hz, J$_2$ = 2.1 Hz, Ar—H), 7.80 (d, 1H, J = 8.1 Hz, Ar—H), 8.65 (d, 1H, J = 8.1 Hz, Ar—H); (CDCl$_3$) | 2922, 1716, 1464, 1433, 1383, 1273, 1223, 1058 |
| 4 | 3.86 (s, 3H, OCH$_3$), 4.50 (t, 2H, CH$_2$), 4.93 (t, 2H, CH$_2$), 6.88 (dd, 1H, J$_1$ = 8.4 Hz, J$_2$ = 2.4 Hz, Ar—H), 7.10 (d, 1H, J = 9.3 Hz, Ar—H), 7.17 (d, 2H, J = 2.4 Hz, Ar—H), 7.41 (d, 1H, J = 8.1 Hz, Ar—H), 7.47 (d, 1H, J = 8.1 Hz, Ar—H), 7.54-7.60 (m, 1H, Ar—H), 7.65 (d, 1H, J = 8.7 Hz, Ar—H), 7.76 (d, 1H, J = 8.1 Hz, Ar—H), 8.64 (d, 1H, J = 8.1 Hz, Ar—H); (CDCl$_3$) | 2960, 1703, 1477, 1436, 1384, 1276, 1224, 1047 |
| 5 | 2.68 (s, 4H, CH$_2$), 2.98 (t, 2H, CH$_2$), 3.78 (t, 4H, CH$_2$), 3.88 (s, 3H, OCH$_3$), 4.79 (t, 2H, CH$_2$), 6.93 (dd, 1H, J$_1$ = 8.1 Hz, J$_2$ = 2.4 Hz, Ar—H), 7.21 (d, 1H, J = 2.4 Hz, Ar—H), 7.42-7.48 (m, 1H, Ar—H), 7.56 (ddd, 1H, J$_1$ = 9.9 Hz, J$_2$ = 8.4 Hz, J$_3$ = 1.5 Hz, Ar—H), 7.70 (d, 1H, J = 8.4 Hz, Ar—H), 7.78 (d, 1H, J = 7.8 Hz, Ar—H), 8.65 (dd, 1H, J$_1$ = 8.4 Hz, J$_2$ = 1.2 Hz, Ar—H); (CDCl$_3$) | 2938, 1710, 1480, 1434, 1383, 1275, 1213, 1039 |
| 6 | 2.30 (t, 2H, CH$_2$), 2.57 (s, 6H, N(CH$_3$)$_2$), 2.86-2.88 (m, 2H, CH$_2$), 3.88 (s, 3H, OCH$_3$), 4.71 (t, 2H, CH$_2$), 6.94 (dd, 1H, J$_1$ = 8.1 Hz, J$_2$ = 2.4 Hz, Ar—H), 7.20 (t, 1H, Ar—H), 7.42-7.48 (m, 1H, Ar—H), 7.57 (ddd, 1H, J$_1$ = 8.4 Hz, J$_2$ = 6.9 Hz, J$_3$ = 1.5 Hz, Ar—H), 7.67 (d, 1H, J = 8.1 Hz, Ar—H), 7.78 (d, 1H, J = 8.4 Hz, Ar—H), 8.65 (dd, 1H, J$_1$ = 8.1 Hz, J$_2$ = 1.2 Hz, Ar—H); (CDCl$_3$) | 2922, 1711, 1463, 1434, 1384, 1272, 1224, 1055 |
| 7 | 2.43 (s, 6H, N(CH$_3$)$_2$), 2.93 (t, 2H, CH$_2$), 4.76 (t, 2H, CH$_2$), 7.41-7.49 (m, 2H, Ar—H), 7.58 (dd, 1H, J$_1$ = 7.2 Hz, J$_2$ = 1.5 Hz, Ar—H), 7.63 (dd, 1H, J$_1$ = 7.2 Hz, J$_2$ = 1.5 Hz, Ar—H), 7.73 (d, 1H, J = 7.8 Hz, Ar—H), 7.81 (d, 1H, J = 8.4 Hz, Ar—H), 8.64 (dd, 1H, J$_1$ = 8.1 Hz, J$_2$ = 1.5 Hz, Ar—H); (CDCl$_3$) | 2960, 2926, 1714, 1460, 1431, 1384, 1172, 1056 |
| 8 | 1.13 (t, 6H, N(CH$_3$)$_2$), 2.71 (q, 4H, CH$_2$), 3.02 (t, 2H, CH$_2$), 4.73 (t, 2H, CH$_2$), 7.43 (dd, 1H, J$_1$ = 7.8 Hz, J$_2$ = 2.1 Hz, Ar—H), 7.48 (dd, 1H, J$_1$ = 8.4 Hz, J$_2$ = 1.2 Hz, Ar—H), 7.58 (t, 1H, Ar—H), 7.63 (dd, 1H, J$_1$ = 6.9 Hz, J$_2$ = 1.5 Hz, Ar—H), 7.77 (d, 1H, J = 8.1 Hz, Ar—H), 7.81 (d, 1H, J = 8.4 Hz, Ar—H), 8.65 (dd, 1H, J$_1$ = 8.1 Hz, J$_2$ = 1.5 Hz, Ar—H); (CDCl$_3$) | 2965, 2929, 1723, 1459, 1411, 1362, 1174, 1057 |
| 9 | 1.86-1.87 (m, 4H, CH$_2$), 2.75 (s, 4H, CH$_2$), 3.11 (t, 2H, CH$_2$), 4.84 (t, 2H, CH$_2$), 7.43-7.50 (m, 2H, Ar—H), 7.60 (d, 1H, J = 1.5 Hz, Ar—H), 7.63 (d, 1H, J = 7.2 Hz, Ar—H), 7.78 (d, 1H, J = 8.1 Hz, Ar—H), 7.83 (d, 1H, J = 8.7 Hz, Ar—H), 8.67 (d, 1H, J = 8.1 Hz, Ar—H); (CDCl$_3$) | 2962, 2925, 1718, 1459, 1432, 1384, 1171, 1056 |
| 10 | 4.52 (t, 2H, CH$_2$), 4.97 (t, 2H, CH$_2$), 7.08 (t, 1H, Ar—H), 7.12 (t, 1H, Ar—H), 7.39 (dd, 1H, J$_1$ = 8.1 Hz, J$_2$ = 1.8 Hz, Ar—H), 7.48 (dt, 1H, J$_1$ = 6.9 Hz, J$_2$ = 1.5 Hz, Ar—H), 7.51 (d, 1H, J = 1.2 Hz, Ar—H), 7.56 (d, 1H, J = 1.8 Hz, Ar—H), 7.62 (ddd, 1H, J$_1$ = 8.4 Hz, J$_2$ = 6.9 Hz, J$_3$ = 1.5 Hz, Ar—H), 7.67 (s, 1H, Ar—H), 7.78 (dd, 1H, J$_1$ = 8.4 Hz, J$_2$ = 0.9 Hz, Ar—H), 8.66 (d, 1H, J = 8.1 Hz, Ar—H); (CDCl$_3$) | 2956, 2923, 1719, 1458, 1428, 1384, 1237, 1053 |
| 11 | 1.50-1.54 (m, 2H, CH$_2$), 1.63-1.71 (m, 4H, CH$_2$), 2.64-2.65 (m, 4H, CH$_2$), 2.96 (t, 2H, CH$_2$), 4.80 (t, 2H, CH$_2$), 7.43-7.50 (m, 2H, Ar—H), 7.58-7.65 (m, 2H, Ar—H), 7.76-7.83 (m, 2H, Ar—H), 8.64 (d, 1H, J = 1.5 Hz, Ar—H); (CDCl$_3$) | 2938, 1713, 1464, 1431, 1384, 1287, 1209, 1054 |
| 12 | 2.35-2.44 (m, 2H, CH$_2$), 2.73 (s, 6H, N(CH$_3$)$_2$), 2.93-2.97 (m, 2H, CH$_2$), 4.75 (t, 2H, CH$_2$), 7.47-7.52 (m, 1H, Ar—H), 7.58-7.62 (m, 1H, Ar—H), 7.72-7.77 (m, 2H, J = 7.8 Hz, Ar—H), 7.82 (d, 1H, J = 8.4 Hz, Ar—H), 8.49 (s, 1H, Ar—H), 8.68 (d, 1H, J = 9.0 Hz, Ar—H); (CDCl$_3$) | 2959, 2921, 1716, 1460, 1431, 1384, 1291, 1210, 1055 |
| 13 | 2.68 (s, 6H, N(CH$_3$)$_2$), 3.28 (t, 2H, CH$_2$), 3.88 (s, 3H, OCH$_3$), 3.96 (s, 3H, OCH$_3$), 4.91 (t, 2H, CH$_2$), 6.94 (dd, 1H, J$_1$ = 8.1 Hz, J$_2$ = 2.7 Hz, Ar—H), 7.20 (d, 1H, J = 2.4 Hz, Ar—H), 7.23 (dd, 1H, J$_1$ = 9.3 Hz, J$_2$ = 3.0 Hz, Ar—H), 7.66 (d, 1H, J = 8.1 Hz, Ar—H), 7.68 (d, 1H, J = 9.3 Hz, Ar—H), 8.01 (d, 1H, J = 2.7 Hz, Ar—H); (CDCl$_3$) | 2924, 1707, 1474, 1432, 1384, 1274, 1212, 1054 |
| 14 | 1.21 (t, 6H, N(CH$_3$)$_2$), 2.88 (t, 4H, J = 7.2 Hz, CH$_2$), 3.20 (d, 2H, J = 4.2 Hz, CH$_2$), 3.87 (s, 3H, OCH$_3$), 3.95 (s, 3H, OCH$_3$), 4.82 (t, 2H, CH$_2$), 6.92 (dd, 1H, J$_1$ = 8.4 Hz, J$_2$ = 2.7 Hz, Ar—H), 7.19 (d, 1H, J = 2.4 Hz, Ar—H), 7.30 (d, 1H, J = 2.7 Hz, Ar—H), 7.66 (d, 1H, J = 9.3 Hz, Ar—H), 7.68 (d, 1H, J = 8.1 Hz, Ar—H), 7.99 (d, 1H, J = 2.7 Hz, Ar—H); (CDCl$_3$) | 2960, 2920, 1709, 1485, 1462, 1373, 1277, 1213, 1024 |
| 15 | 1.55-1.59 (m, 2H, CH$_2$), 1.78-1.80 (m, 4H, CH$_2$), 2.82-2.87 (m, 4H, CH$_2$), 3.18 (t, 2H, CH$_2$), 3.88 (s, 3H, OCH$_3$), 3.96 (s, 3H, OCH$_3$), 4.90 (t, 2H, CH$_2$), 6.93 (dd, 1H, J$_1$ = 8.1 Hz, J$_2$ = 2.4 Hz, Ar—H), 7.18 (d, 1H, J = 2.4 Hz, Ar—H), 7.22 (dd, 1H, J$_1$ = 9.3 Hz, J$_2$ = 3.0 Hz, Ar—H), 7.67 (d, 2H, J = 9.0 Hz, Ar—H), 8.00 (d, 1H, J = 3.0 Hz, Ar—H); (CDCl$_3$) | 2923, 1710, 1475, 1428, 1371, 1219, 1024 |
| 16 | 2.58 (t, 2H, CH$_2$), 2.87 (s, 6H, N(CH$_3$)$_2$), 3.28 (t, 2H, CH$_2$), 3.87 (s, 3H, OCH$_3$), 3.95 (s, 3H, OCH$_3$), 4.71 (t, 2H, CH$_2$), 6.97 (dd, 1H, J$_1$ = 8.4 Hz, J$_2$ = 2.4 Hz, Ar—H), 7.19 (dd, 1H, J$_1$ = 6.0 Hz, J$_2$ = 2.7 Hz, Ar—H), 7.23 (d, 1H, J = 2.7 Hz, Ar—H), 7.65 (d, 2H, J = 9.3 Hz, Ar—H), 7.98 (d, 1H, J = 5.7 Hz, Ar—H); (CDCl$_3$) | 2922, 1713, 1466, 1384, 1275, 1216, 1026 |
| 17 | 2.45 (s, 6H, N(CH$_3$)$_2$), 2.93 (t, 2H, CH$_2$), 3.95 (s, 3H, OCH$_3$), 3.98 (s, 3H, OCH$_3$), 4.75 (t, 2H, CH$_2$), 6.71 (dd, 1H, J$_1$ = 8.4 Hz, J$_2$ = 2.4 Hz, Ar—H), 7.25 (d, 1H, J = 3.0 Hz, Ar—H), 7.45 (d, 1H, J = 2.4 Hz, Ar—H), 7.60 (d, 1H, J = 8.1 Hz, Ar—H), 7.72 (d, 1H, J = 9.0 Hz, Ar—H), 8.10 (d, 1H, J = 2.7 Hz, Ar—H); (CDCl$_3$) | 2925, 1699, 1487, 1432, 1384, 1289, 1225, 1044 |
| 18 | 1.83-1.87 (m, 4H, CH$_2$), 2.74 (s, 4H, CH$_2$), 3.09 (t, 2H, CH$_2$), 3.97 (s, 3H, OCH$_3$), 4.79 (t, 2H, CH$_2$), 7.28 (t, 1H, Ar—H), 7.60 (dd, 1H, J$_1$ = 7.8 Hz, J$_2$ = 1.8 Hz, Ar—H), 7.70 (d, 1H, J = 1.2 Hz, Ar—H), 7.72 (d, 2H, J = 1.5 Hz, Ar—H), 8.00 (d, 1H, J = 3.0 Hz, Ar—H); (CDCl$_3$) | 2960, 2922, 1714, 1459, 1384, 1293, 1211, 1026 |
| 19 | 3.86 (s, 3H, OCH$_3$), 4.54 (t, 2H, CH$_2$), 4.78 (t, 2H, CH$_2$), 6.92 (s, 1H, Ar—H), 7.32 (dd, 2H, J$_1$ = 9.0 Hz, J$_2$ = 2.1 Hz, Ar—H), 7.49 (d, 1H, J = 7.8 Hz, Ar—H), 7.62 (d, 2H, J = 8.4 Hz, Ar—H), 7.74 (d, 1H, J = 7.8 Hz, Ar—H), 7.81 (d, 1H, J = 2.7 Hz, Ar—H), 7.83 (s, 1H, Ar—H); (DMSO-d$_6$) | 2956, 2924, 1716, 1449, 1384, 1286 |
| 20 | 2.80 (s, 6H, N(CH$_3$)$_2$), 3.40 (t, 2H, CH$_2$), 3.87 (s, 3H, OCH$_3$), 4.02 (s, 3H, OCH$_3$), 4.05 (s, 3H, | 2937, 1707, 1463, 1426, |

TABLE 2-continued

The $^1$H-NMR spectra and mass spectra data of the target compounds of formula (Ia)

| Compound No. | $^1$H NMR (300 MHz) | IR $v_{max}$ cm$^{-1}$ |
|---|---|---|
|  | OCH$_3$), 5.00 (t, 2H, CH$_2$), 6.91-6.95 (m, 1H, Ar—H), 7.12 (s, 1H, Ar—H), 7.17 (d, 1H, J = 2.4 Hz, Ar—H), 7.58 (d, 1H, J = 7.5 Hz, Ar—H), 7.96 (s, 1H, Ar—H); (CDCl$_3$) | 1384, 1276, 1213, 1031 |
| 21 | 1.18-1.27 (m, 6H, N(CH$_3$)$_2$), 2.85 (q, 4H, CH$_2$), 3.17 (s, 2H, CH$_2$), 3.87 (s, 3H, OCH$_3$), 4.01 (s, 3H, OCH$_3$), 4.04 (s, 3H, OCH$_3$), 4.78 (s, 2H, CH$_2$), 6.92 (dd, 1H, J$_1$ = 8.1 Hz, J$_2$ = 2.4 Hz, Ar—H), 7.14 (s, 1H, Ar—H), 7.17 (d, 1H, J = 2.4 Hz, Ar—H), 7.63 (d, 1H, J = 8.1 Hz, Ar—H), 7.97 (s, 1H, Ar—H); (CDCl$_3$) | 2924, 1716, 1486, 1462, 1384, 1278, 1249, 1025 |
| 22 | 1.89-1.93 (m, 4H, CH$_2$), 2.86 (s, 4H, CH$_2$), 3.20 (t, 2H, CH$_2$), 3.88 (s, 3H, OCH$_3$), 4.02 (s, 3H, OCH$_3$), 4.05 (s, 3H, OCH$_3$), 4.83 (t, 2H, CH$_2$), 6.93 (dd, 1H, J$_1$ = 8.1 Hz, J$_2$ = 2.4 Hz, Ar—H), 7.15 (s, 1H, Ar—H), 7.18 (d, 1H, J = 2.4 Hz, Ar—H), 7.65 (d, 1H, J = 8.1 Hz, Ar—H), 7.98 (s, 1H, Ar—H); (CDCl$_3$) | 2924, 1709, 1499, 1483, 1384, 1276, 1246, 1030 |
| 23 | 2.68 (s, 4H, CH$_2$), 2.99 (d, 2H, J = 6.0 Hz, CH$_2$), 3.77 (t, 4H, CH$_2$), 3.88 (s, 3H, OCH$_3$), 4.02 (s, 3H, OCH$_3$), 4.05 (s, 3H, OCH$_3$), 4.74 (t, 2H, CH$_2$), 6.93 (dd, 1H, J$_1$ = 8.1 Hz, J$_2$ = 2.4 Hz, Ar—H), 7.14 (s, 1H, Ar—H), 7.18 (d, 1H, J = 2.4 Hz, Ar—H), 7.66 (d, 1H, J = 8.1 Hz, Ar—H), 7.99 (s, 1H, Ar—H); (CDCl$_3$) | 2965, 2924, 1709, 1483, 1383, 1276, 1217, 1031 |
| 24 | 1.50-1.52 (m, 2H, CH$_2$), 1.66-1.74 (m, 4H, CH$_2$), 2.70 (s, 4H, CH$_2$), 3.03 (t, 2H, CH$_2$), 3.86 (s, 3H, OCH$_3$), 4.00 (s, 3H, OCH$_3$), 4.04 (s, 3H, OCH$_3$), 4.76 (t, 2H, CH$_2$), 6.91 (dd, 1H, J$_1$ = 8.1 Hz, J$_2$ = 2.4 Hz, Ar—H), 7.12 (d, 1H, J = 3.6 Hz, Ar—H), 7.15 (d, 1H, J = 2.4 Hz, Ar—H), 7.62 (d, 1H, J = 8.1 Hz, Ar—H), 7.94 (s, 1H, Ar—H); (CDCl$_3$) | 2924, 1711, 1495, 1483, 1384, 1277, 1249, 1026 |
| 25 | 2.21-2.26 (m, 2H, CH$_2$), 2.47 (s, 6H, N(CH$_3$)$_2$), 2.76 (t, 2H, CH$_2$), 3.86 (s, 3H, OCH$_3$), 4.00 (s, 3H, OCH$_3$), 4.04 (s, 3H, OCH$_3$), 4.62 (t, 2H, CH$_2$), 6.91 (dd, 1H, J$_1$ = 8.1 Hz, J$_2$ = 2.4 Hz, Ar—H), 7.11 (s, 1H, Ar—H), 7.15 (d, 1H, J = 2.7 Hz, Ar—H), 7.59 (d, 1H, J = 8.4 Hz, Ar—H), 7.95 (s, 1H, Ar—H); (CDCl$_3$) | 2923, 1709, 1494, 1384, 1278, 1028 |
| 26 | 2.44 (s, 6H, N(CH$_3$)$_2$), 2.92 (t, 2H, CH$_2$), 4.04 (s, 3H, OCH$_3$), 4.06 (s, 3H, OCH$_3$), 4.72 (t, 2H, CH$_2$), 7.15 (s, 1H, Ar—H), 7.41 (dd, 1H, J$_1$ = 8.1 Hz, J$_2$ = 2.1 Hz,, Ar—H), 7.54 (d, 1H, J = 2.1 Hz, Ar—H), 7.68 (d, 1H, J = 7.8 Hz, Ar—H), 7.96 (s, 1H, Ar—H); (CDCl$_3$) | 2923, 1712, 1496, 1383, 1294, 1213, 1032 |
| 27 | 4.04 (s, 3H, OCH$_3$), 4.06 (s, 3H, OCH$_3$), 4.53 (t, 2H, CH$_2$), 4.94 (t, 2H, CH$_2$), 7.09 (s, 1H, Ar—H), 7.14 (s, 2H, Ar—H), 7.42 (d, 1H, J = 1.8 Hz, Ar—H), 7.46 (d, 1H, J = 7.8 Hz, Ar—H), 7.56 (d, 1H, J = 1.8 Hz, Ar—H), 7.77 (s, 1H, Ar—H), 7.98 (s, 1H, Ar—H); (CDCl$_3$) | 2924, 1714, 1497, 1455, 1385, 1250, 1215, 1031 |
| 28 | 2.68 (s, 4H, CH$_2$), 2.98 (t, 2H, CH$_2$), 3.78 (t, 4H, CH$_2$), 4.05 (s, 3H, OCH$_3$), 4.07 (s, 3H, OCH$_3$), 4.76 (t, 2H, CH$_2$), 7.17 (s, 1H, Ar—H), 7.40 (dd, 1H, J$_1$ = 7.8 Hz, J$_2$ = 2.1 Hz, Ar—H), 7.58 (d, 1H, J = 1.8 Hz, Ar—H), 7.73 (d, 1H, J = 7.8 Hz, Ar—H), 8.00 (s, 1H, Ar—H); (CDCl$_3$) | 2954, 2923, 1715, 1495, 1384, 1296, 1215, 1032 |
| 29 | 2.24-2.29 (m, 2H, CH$_2$), 2.70 (s, 6H, N(CH$_3$)$_2$), 3.15 (t, 2H, CH$_2$), 3.82 (s, 3H, OCH$_3$), 3.85 (s, 3H, OCH$_3$), 4.51 (t, 2H, CH$_2$), 6.97 (d, 1H, J = 2.7 Hz, Ar—H), 7.30-7.35 (m, 2H, Ar—H), 7.48 (d, 1H, J = 7.8 Hz, Ar—H), 7.74 (d, 1H, J = 2.7 Hz, Ar—H); (CDCl$_3$ + one drop of CH$_3$OH) | 2960, 1712, 1500, 1385, 1362, 1255, 1057 |
| 30 | 3.87 (s, 3H, OCH$_3$), 4.97 (t, 2H, CH$_2$), 5.35 (t, 2H, CH$_2$), 6.92-6.96 (m, 1H, Ar—H), 7.19 (d, 1H, J = 2.7 Hz, Ar—H), 7.31-7.34 (m, 2H, Ar—H), 7.51 (d, 1H, J = 5.7 Hz, Ar—H), 8.00 (dd, 1H, J$_1$ = 8.1 Hz, J$_2$ = 0.3 Hz, Ar—H), 8.67-8.70 (m, 1H, Ar—H); (CDCl$_3$) | 2941, 1719, 1477, 1433, 1384, 1032 |

The chemical structures of the target products of formula (II) synthesized in the present invention are shown in Table 3. The chemical structures of the target products were systematically characterized by $^1$H-NMR, MS, IR and melting point. The specific data are shown in Table 3 and 4.

TABLE 3 the structures of the compounds of formula (IIa)

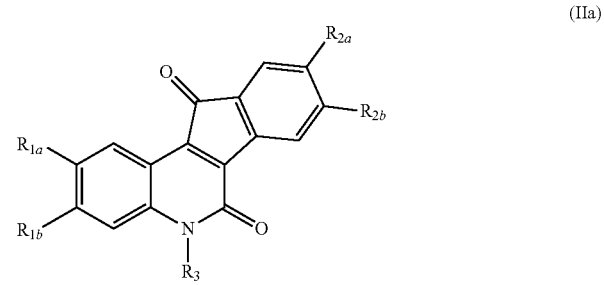

(IIa)

| Compound No. | R$_{1a}$ | R$_{1b}$ | R$_{2a}$ | R$_{2b}$ | R$_3$ | melting point/° C. | MS (m/z) |
|---|---|---|---|---|---|---|---|
| 31 | H | H | OCH$_3$ | H | CH$_2$CH$_2$N(CH$_3$)$_2$ | 198-200 | 349.8 (MH$^+$, 100) |
| 32 | H | H | OCH$_3$ | H | CH$_2$CH$_2$N(pyrrolidine) | 181-183 | 375.2 ((MH$^+$, 100) |

TABLE 3-continued the structures of the compounds of formula (IIa)

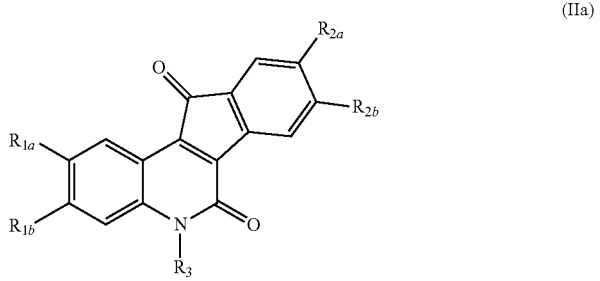

(IIa)

| Compound No. | $R_{1a}$ | $R_{1b}$ | $R_{2a}$ | $R_{2b}$ | $R_3$ | melting point/°C. | MS (m/z) |
|---|---|---|---|---|---|---|---|
| 33 | H | H | OCH$_3$ | H | CH$_2$CH$_2$N(morpholine) | 220-222 | 391.5 (MH$^+$, 100) |
| 34 | H | H | OCH$_3$ | H | CH$_2$CH$_2$CH$_2$N(CH$_3$)$_2$ | 180-182 | 363.5 (MH$^+$, 100) |
| 35 | H | H | Cl | H | CH$_2$CH$_2$N(CH$_3$)$_2$ | 192-194 | 353.3 (MH$^+$, 100) |
| 36 | H | H | Cl | H | CH$_2$CH$_2$N(CH$_2$CH$_3$)$_2$ | 151-153 | 382.3 (MH$^+$, 100) |
| 37 | H | H | Cl | H | CH$_2$CH$_2$N(pyrrolidine) | 209-211 | 379.5 (MH$^+$, 100) |
| 38 | H | H | Cl | H | CH$_2$CH$_2$N(imidazole) | 287 (dec) | 376.8 (MH$^+$, 100) |
| 39 | H | H | Cl | H | CH$_2$CH$_2$N(piperidine) | 207-209 | 393.3 (MH$^+$, 100) |
| 40 | H | H | Cl | H | CH$_2$CH$_2$CH$_2$N(CH$_3$)$_2$ | 262-264 | 367.4 (MH$^+$, 100) |
| 41 | OCH$_3$ | H | OCH$_3$ | H | CH$_2$CH$_2$N(CH$_3$)$_2$ | 202-204 | 379.4 (MH$^+$, 100) |
| 42 | OCH$_3$ | H | H | OCH$_3$ | CH$_2$CH$_2$N(CH$_3$)$_2$ | 196-198 | 379.5 (MH$^+$, 100) |
| 43 | OCH$_3$ | H | Br | H | CH$_2$CH$_2$N(imidazole) | 232-234 | 450.2 ((MH$^+$, 100) |
| 44 | OCH$_3$ | OCH$_3$ | OCH$_3$ | H | CH$_2$CH$_2$N(pyrrolidine) | 256-258 | 435.3 (MH$^+$, 100) |
| 45 | OCH$_3$ | OCH$_3$ | OCH$_3$ | H | CH$_2$CH$_2$N(morpholine) | 231-233 | 451.4 (MH$^+$, 100) |
| 46 | OCH$_3$ | OCH$_3$ | OCH$_3$ | H | CH$_2$CH$_2$CH$_2$N(CH$_3$)$_2$ | 270 (dec) | 423.4 (MH$^+$, 100) |
| 47 | OCH$_3$ | OCH$_3$ | Cl | H | CH$_2$CH$_2$N(CH$_3$)$_2$ | 280 (dec) | 413.4 (MH$^+$, 100) |
| 48 | OCH$_3$ | OCH$_3$ | Cl | H | CH$_2$CH$_2$N(imidazole) | 280 (dec) | 436.2 (MH$^+$, 100) |
| 49 | OCH$_3$ | OCH$_3$ | Cl | H | CH$_2$CH$_2$N(morpholine) | 258-260 | 455.4 (MH$^+$, 100) |
| 50 | OCH$_3$ | OCH$_3$ | Cl | H | CH$_2$CH$_2$CH$_2$N(CH$_3$)$_2$ | 201-203 | 427.5 (MH$^+$, 100) | dec = decomposition

Compounds 31-50 were prepared in Examples 31-50, respectively.

TABLE 4

The $^1$H-NMR spectra and mass spectra data of the compounds of formula (IIa)

| Compound No. | $^1$H NMR (300 MHz) | IR $v_{max}$ cm$^{-1}$ |
|---|---|---|
| 31 | 2.45 (s, 6H, N(CH$_3$)$_2$), 2.70 (t, 2H, CH$_2$), 3.87 (s, 3H, OCH$_3$), 4.55 (t, 2H, CH$_2$), 6.93 (dd, 1H, J$_1$ = 8.1 Hz, J$_2$ = 2.4 Hz, Ar—H), 7.18 (d, 1H, J = 2.4 Hz, Ar—H), 7.29-7.34 (m, 1H, Ar—H), 7.46 (d, 1H, J = 8.7 Hz, Ar—H), 7.54-7.60 (m, 1H, Ar—H), 7.98 (d, 1H, J = 8.1 Hz, Ar—H), 8.69 (dd, 1H, J$_1$ = 8.4 Hz, J$_2$ = 1.5 Hz, Ar—H); (CDCl$_3$) | 2967, 2922, 1720, 1654, 1479, 1433, 1384, 1226, 1044 |
| 32 | 1.83-1.92 (m, 4H, CH$_2$), 2.76 (t, 4H, CH$_2$), 2.87 (t, 2H, CH$_2$), 3.87 (s, 3H, OCH$_3$), 4.59 (t, 2H, CH$_2$), 6.93 (dd, 1H, J$_1$ = 8.1 Hz, J$_2$ = 2.4 Hz, Ar—H), 7.18 (t, 1H, Ar—H), 7.29-7.34 (m, 1H, Ar—H), 7.44-7.59 (m, 2H, Ar—H), 7.99 (d, 1H, J = 8.1 Hz, Ar—H), 8.69 (dd, 1H, J$_1$ = 8.1 Hz, J$_2$ = 1.5 Hz, Ar—H); (CDCl$_3$) | 2962, 1719, 1651, 1477, 1384, 1224, 1186, 1041 |
| 33 | 2.61 (br, 4H, CH$_2$), 2.68-2.75 (m, 2H, CH$_2$), 3.78 (br, 4H, CH$_2$), 3.87 (s, 3H, OCH$_3$), 4.54(t, 2H, CH$_2$), 6.93 (dd, 1H, J$_1$ = 8.1 Hz, J$_2$ = 2.4 Hz, Ar—H), 7.18 (d, 1H, J = 2.4 Hz, Ar—H), 7.30-7.35 (m, 1H, Ar—H), 7.55 (d, 1H, J = 8.1 Hz, Ar—H), 7.57 (t, 1H, Ar—H), 7.98 (d, 1H, J = 8.1 Hz, Ar—H), 8.69 (d, 1H, J = 8.1 Hz, Ar—H); (CDCl$_3$) | 2961, 2932, 1720, 1650, 1478, 1384, 1223, 1045 |
| 34 | 2.00-2.02 (m, 2H, CH$_2$), 2.34 (s, 6H, N(CH$_3$)$_2$), 2.54 (t, 2H, CH$_2$), 3.87 (s, 3H, OCH$_3$), 4.46 (t, 2H, CH$_2$), 6.93 (dd, 1H, J$_1$ = 8.1 Hz, J$_2$ = 2.4 Hz, Ar—H), 7.18 (t, 1H, Ar—H), 7.31-7.33 (m, 1H, Ar—H), 7.51-7.56 (m, 2H, Ar—H), 7.99 (d, 1H, J = 8.1 Hz, Ar—H), 8.69 (d, 1H, J = 7.8 Hz, Ar—H); (CDCl$_3$) | 2919, 1717, 1650, 1478, 1434, 1383, 1225, 1055 |
| 35 | 2.43 (s, 6H, N(CH$_3$)$_2$), 2.69 (t, 2H, CH$_2$), 4.54 (t, 2H, CH$_2$), 7.31-7.37 (m, 1H, Ar—H), 7.44-7.49 (m, 2H, Ar—H), 7.55 (d, 1H, J = 1.8 Hz, Ar—H), 7.59-7.65 (m, 1H, Ar—H), 8.06 (d, 1H, J = 8.1 Hz, Ar—H), 8.69 (dd, 1H, J$_1$ = 8.1 Hz, J$_2$ = 1.2 Hz, Ar—H); (CDCl$_3$) | 2972, 2923, 1720, 1650, 1384, 1230, 1172, 1051 |
| 36 | 1.09-1.18 (m, 6H, N(CH$_3$)$_2$), 2.70-2.77 (m, 4H, CH$_2$), 2.82 (t, 2H, CH$_2$), 4.50 (t, 2H, CH$_2$), 7.31-7.36 (m, 1H, Ar—H), 7.45-7.48 (m, 2H, Ar—H), 7.51-7.57 (m, 1H, Ar—H), 7.59-7.65 (m, 1H, Ar—H), 8.06 (d, 1H, J = 7.8 Hz, Ar—H), 8.68 (d, 1H, J = 7.8 Hz, Ar—H); (CDCl$_3$) | 2962, 2925, 1716, 1652, 1384, 1231, 1170, 1051 |
| 37 | 1.87-1.91 (m, 4H, CH$_2$), 2.75-2.79 (m, 4H, CH$_2$), 2.87 (t, 2H, CH$_2$), 4.58 (t, 2H, CH$_2$), 7.33-7.37 (m, 1H, Ar—H), 7.46 (d, 1H, J = 2.1 Hz, Ar—H), 7.49-7.50 (m, 1H, Ar—H), 7.53-7.56 (m, 1H, Ar—H), 7.60-7.63 (m, 1H, Ar—H), 8.07 (d, 1H, J = 7.8 Hz, Ar—H), 8.70 (dd, 1H, J$_1$ = 8.1 Hz, J$_2$ = 0.9 Hz, Ar—H); (CDCl$_3$) | 1956, 2925, 1720, 1650, 1384, 1173, 1071 |
| 38 | 4.42 (t, 2H, CH$_2$), 4.73 (t, 2H, CH$_2$), 6.99 (s, 1H, Ar—H), 7.06-7.12 (m, 2H, Ar—H), 7.31-7.39 (m, 2H, Ar—H), 7.48-7.60 (m, 3H, J$_1$ = 6.9 Hz, J$_2$ = 1.5 Hz, Ar—H), 8.04 (d, 1H, J = 7.8 Hz, Ar—H), 8.73 (d, 1H, J = 9.0 Hz, Ar—H); (CDCl$_3$) | 2923, 1724, 1656, 1484, 1384, 1211, 1170 |
| 39 | 1.46-1.52 (m, 2H, CH$_2$), 1.61-1.68 (m, 4H, CH$_2$), 2.60 (t, 4H, CH$_2$), 2.65-2.70 (m, 2H, CH$_2$), 4.52 (t, 2H, CH$_2$), 7.30-7.33 (m, 1H, Ar—H), 7.41-7.45 (m, 1H, Ar—H), 7.48 (s, 1H, Ar—H), 7.50-7.51 (m, 1H, Ar—H), 7.55-7.61 (m, 1H, Ar—H), 8.02 (d, 1H, J = 7.8 Hz, Ar—H), 8.64 (dd, 1H, J$_1$ = 8.1 Hz, J$_2$ = 1.5 Hz, Ar—H); (CDCl$_3$) | 2936, 1721, 1646, 1446, 1384, 1216, 1172, 1042 |
| 40 | 2.28-2.33 (m, 2H, CH$_2$), 2.82 (s, 6H, N(CH$_3$)$_2$), 3.21-3.27 (m, 2H, CH$_2$), 4.47 (t, 2H, CH$_2$), 7.30-7.35 (m, 1H, Ar—H), 7.42 (dd, 1H, J$_1$ = 8.1 Hz, J$_2$ = 1.8 Hz, Ar—H), 7.51 (d, 1H, J = 1.8 Hz, Ar—H), 7.55-7.58 (m, 1H, Ar—H), 7.63 (dd, 1H, J$_1$ = 7.2 Hz, J$_2$ = 1.5 Hz, Ar—H), 7.92 (d, 1H, J = 7.8 Hz, Ar—H), 8.63 (dd, 1H, J$_1$ = 8.1 Hz, J$_2$ = 1.2 Hz, Ar—H); (CDCl$_3$) | 2960, 2921, 1724, 1650, 1384, 1228, 1170, 1044 |
| 41 | 2.44 (s, 6H, N(CH$_3$)$_2$), 2.69 (t, 2H, CH$_2$), 3.89 (s, 3H, OCH$_3$), 3.94 (s, 3H, OCH$_3$), 4.53 (t, 2H, CH$_2$), 6.94 (dd, 1H, J$_1$ = 8.1 Hz, J$_2$ = 2.4 Hz, Ar—H), 7.17-7.22 (m, 2H, Ar—H), 7.39 (d, 1H, J = 9.3 Hz, Ar—H), 8.02 (d, 1H, J = 8.1 Hz, Ar—H), 8.17 (d, 1H, J = 2.7 Hz, Ar—H); (CDCl$_3$) | 2925, 1712, 1648, 1458, 1384, 1273, 1223, 1040 |
| 42 | 2.72 (s, 6H, N(CH$_3$)$_2$), 3.04 (t, 2H, CH$_2$), 3.91 (s, 3H, OCH$_3$), 3.93 (s, 3H, OCH$_3$), 4.70 (t, 2H, CH$_2$), 6.69 (d, 1H, J = 2.1 Hz, Ar—H), 7.65-7.60 (m, 2H, Ar—H), 7.72 (d, 1H, J = 6.6 Hz, Ar—H), 8.27 (d, 1H, J = 1.5 Hz, Ar—H), 8.48 (s, 1H, Ar—H); (CDCl$_3$) | 2923, 1731, 1684, 1473, 1384, 1228 |
| 43 | 3.87 (s, 3H, OCH$_3$), 4.35 (t, 2H, CH$_2$), 4.59 (t, 2H, CH$_2$), 6.87-6.90 (m, 2H, Ar—H), 7.04 (d, 1H, J = 1.8 Hz, Ar—H), 7.08-7.12 (m, 1H, Ar—H), 7.34-7.42 (m, 1H, Ar—H), 7.47-7.61 (m, 2H, Ar—H), 7.82-8.00 (m, 1H, Ar—H), 8.04 (s, 1H, Ar—H); (CDCl$_3$) | 2959, 2922, 1714, 1641, 1384, 1278, 1238, 1038 |
| 44 | 2.02-2.06 (m, 4H, CH$_2$), 2.92-2.94 (m, 2H, CH$_2$), 3.07-3.09 (m, 4H, CH$_2$), 3.86 (s, 3H, OCH$_3$), 4.01 (s, 3H, OCH$_3$), 4.11 (s, 3H, OCH$_3$), 4.75 (t, 2H, CH$_2$), 6.90-6.94 (m, 1H, Ar—H), 7.14 (d, 1H, J = 2.1 Hz, Ar—H), 7.17 (t, 1H, Ar—H), 7.88 (d, 1H, J = 8.1 Hz, Ar—H), 8.10 (s, 1H, Ar—H); (CDCl$_3$) | 2923, 1712, 1644, 1477, 1384, 1277, 1221, 1045 |
| 45 | 2.66 (t, 4H, CH$_2$), 2.75 (t, 2H, CH$_2$), 3.77 (t, 4H, CH$_2$), 3.86 (s, 3H, OCH$_3$), 4.01 (s, 3H, OCH$_3$), 4.02 (s, 3H, OCH$_3$), 4.51-4.54 (br, 2H, CH$_2$), 6.92 (dd, 2H, J$_1$ = 8.1 Hz, J$_2$ = 2.7 Hz, Ar—H), 7.13 (d, 1H, J = 2.4 Hz, Ar—H), 7.92 (d, 1H, J = 8.1 Hz, Ar—H), 8.10 (s, 1H, Ar—H); (CDCl$_3$) | 2923, 1715, 1648, 1474, 1384, 1222, 1046 |
| 46 | 2.48-2.50 (m, 2H, CH$_2$), 2.85 (s, 6H, N(CH$_3$)$_2$), 3.26 (t, 2H, CH$_2$), 3.87 (s, 3H, OCH$_3$), 4.00 (s, 3H, OCH$_3$), 4.15 (s, 3H, OCH$_3$), 4.56 (t, 2H, CH$_2$), 6.91 (dd, 2H, J$_1$ = 8.1 Hz, J$_2$ = 2.4 Hz, Ar—H), 7.15 (d, 1H, J = 2.4 Hz, Ar—H), 7.86 (d, 1H, J = 8.1 Hz, Ar—H), 8.11 (s, 1H, Ar—H); (CDCl$_3$) | 2938, 1716, 1684, 1474, 1384, 1221, 1046 |
| 47 | 2.50 (s, 6H, N(CH$_3$)$_2$), 2.76-2.82 (m, 2H, CH$_2$), 4.02 (s, 3H, OCH$_3$), 4.06 (s, 3H, OCH$_3$), 4.55 (t, 2H, CH$_2$), 7.03 (s, 1H, Ar—H), 7.43-7.46 (m, 1H, Ar—H), 7.53 (d, 1H, J = 1.5 Hz, Ar—H), 7.99 (d, 1H, J = 8.1 Hz, Ar—H), 8.11 (s, 1H, Ar—H); (CDCl$_3$) | 2941, 1689, 1487, 1432, 1383, 1289, 1225, 1050 |
| 48 | 4.07 (s, 3H, OCH$_3$), 4.09 (s, 3H, OCH$_3$), 4.34-2.39 (m, 2H, CH$_2$), 4.71 (t, 2H, CH$_2$), 6.90-6.94 (m, 2H, Ar—H), 7.11 (d, 2H, J = 2.1 Hz, Ar—H), 7.17 (t, 2H, Ar—H), 7.88 (d, 1H, J = 7.8 Hz, Ar—H), 8.15 (s, 1H, Ar—H); (CDCl$_3$) | 2948, 2922, 1714, 1648, 1384, 1293, 1041 |
| 49 | 2.65-2.68 (m, 4H, CH$_2$), 2.76 (t, 2H, CH$_2$), 3.77 (t, 4H, CH$_2$), 4.03 (s, 3H, OCH$_3$), 4.05 (s, 3H, OCH$_3$), 4.56 (t, 2H, CH$_2$), 6.94 (s, 1H, Ar—H), 7.46 (dd, 1H, J$_1$ = 8.1 Hz, J$_2$ = 2.1 Hz, Ar—H), 7.53 (d, 1H, J = 2.1 Hz, Ar—H), 7.88 (d, 1H, J = 7.8 Hz, Ar—H), 8.12 (s, 1H, Ar—H); (CDCl$_3$) | 2955, 2923, 1712, 1649, 1467, 1384, 1208, 1033 |
| 50 | 1.91-2.00 (m, 2H, CH$_2$), 2.32 (s, 6H, N(CH$_3$)$_2$), 2.45 (t, 2H, CH$_2$), 4.00 (s, 3H, OCH$_3$), 4.01 (s, 3H, OCH$_3$), 4.41 (t, 2H, CH$_2$), 6.98 (d, 1H, J = 6.0 Hz, Ar—H), 7.42 (dd, 1H, J$_1$ = 8.1 Hz, J$_2$ = 2.1 Hz, Ar—H), 7.47 (dd, 1H, J$_1$ = 2.1 Hz, J$_2$ = 0.6 Hz, Ar—H), 7.95 (d, 1H, J = 0.6 Hz, Ar—H), 8.03 (d, 1H, J = 6.3 Hz, Ar—H); (CDCl$_3$) | 2934, 1716, 1645, 1468, 1384, 1219, 1165, 1057 |

Example 51

The Anti-Tumor Activity Test In Vitro

1. Test Strains:

The tumor cell lines used in the experiments were as follows: A549 (human lung cancer cells), Colo205 (human colon cancer cells), MDA-MB-435 (human breast cancer cells), HepG2 (human hepatoma cells) (purchased from Shanghai Institute of Pharmaceutical Industry).

2. Sample Preparation:

The sample was dissolved in DMSO (Merck), and PBS was added to prepare a 1000 μg/mL of solution or a uniform suspension. And then, DMSO-containing PBS (−) was added to dilute the solution or suspension. The positive control medicament was 10-hydroxycamptothecin (HCPT).

3. Test Method

MTT assay: 100 μL cell suspension (4~5×10$^4$ cells/mL) was added into each well of 96-well plate, and cultured in 37° C., 5% $CO_2$ incubator. After 24 h, the sample solution was added in duplicate, 10 μL/well, and incubated at 37° C., 5% $CO_2$ for 72 h. 20 μL MTT solution (5 mg/mL) was added into each well. After 4 h, a dissolving solution was added, 100 μL/well. The plate was placed into the incubator. After dissolved, OD value at 570 nm was measured on MK-2 automatic microplate reader. (In vitro anti-tumor activities are shown in Table 5 and 6)

TABLE 5

In vitro proliferation inhibiting effects of some samples of Formula (Ia) on human tumor cells

| | A549 | | Colo205 | | MDA-MB-435 | | HepG2 | |
|---|---|---|---|---|---|---|---|---|
| Compound No. | $IC_{50}$ (μg/mL) | 100 μg/mL IC % | $IC_{50}$ (μg/mL) | 100 μg/mL IC % | $IC_{50}$ (μg/mL) | 100 μg/mL IC % | $IC_{50}$ (μg/mL) | 100 μg/mL IC % |
| 1 | 0.983 | 100 | 0.621 | 100 | 1.00 | 95.81 | 0.721 | 99.40 |
| 2 | 1.53 | 100 | 0.427 | 100 | 1.99 | 100 | 2.50 | 100 |
| 3 | 14.39 | 99.90 | 10.97 | 92.33 | 26.55 | 100 | 24.99 | 80.79 |
| 4 | 16.61 | 78.34 | 13.51 | 60.32 | >100 | 48.21 | >100 | 34.87 |
| 5 | >100 | 48.72 | >100 | 43.88 | >100 | 19.75 | >100 | 13.97 |
| 6 | 1.14 | 100 | 0.719 | 100 | 3.64 | 100 | 2.17 | 98.33 |
| 7 | 15.12 | 90.29 | 6.46 | 100 | 4.91 | 100 | 22.95 | 100 |
| 8 | 28.56 | 84.24 | 15.16 | 99.01 | 31.62 | 100 | 28.84 | 73.57 |
| 9 | 5.78 | 100 | 7.10 | 71.11 | 12.28 | 100 | 15.99 | 82.92 |
| 10 | 14.48 | 97.57 | 31.06 | 80.16 | 15.02 | 99.70 | 34.93 | 92.06 |
| 11 | 32.73 | 69.84 | 39.33 | 69.24 | 44.76 | 69.43 | 55.62 | 63.27 |
| 12 | 3.04 | 88.18 | 1.16 | 100 | 0.585 | 100 | 3.19 | 100 |
| 13 | 17.27 | 100 | 1.79 | 96.52 | 4.34 | 100 | 2.47 | 100 |
| 14 | 6.11 | 100 | 0.580 | 97.47 | 1.29 | 99.95 | 0.552 | 100 |
| 15 | 6.95 | 100 | 3.13 | 100 | 6.88 | 99.08 | 5.02 | 100 |
| 16 | 2.91 | 100 | 3.49 | 100 | 4.09 | 100 | 3.48 | 100 |
| 17 | 18.26 | 85.30 | 6.70 | 100 | 4.98 | 100 | 10.31 | 100 |
| 18 | >100 | 35.69 | >100 | 43.88 | 24.86 | 67.72 | >100 | 35.48 |
| 19 | >100 | 17.66 | 18.70 | 80.89 | 42.24 | 59.37 | >100 | 37.50 |
| 20 | 13.78 | 100 | 0.606 | 93.79 | 0.99 | 99.28 | 1.28 | 99.17 |
| 21 | 1.68 | 100 | 2.56 | 88.97 | 1.17 | 93.41 | 0.700 | 93.16 |
| 22 | 1.43 | 97.05 | 1.30 | 93.84 | 1.85 | 100 | 8.61 | 81.69 |
| 24 | 10.32 | 93.92 | 5.15 | 98.38 | 8.92 | 90.85 | 10.78 | 98.55 |
| 25 | 2.02 | 100 | 1.15 | 90.36 | 2.66 | 85.38 | 1.58 | 89.70 |
| 26 | 6.89 | 100 | 1.45 | 100 | 10.51 | 100 | 11.27 | 97.91 |
| 27 | >100 | 35.12 | 25.50 | 66.27 | 91.52 | 51.23 | 56.61 | 57.51 |
| 29 | 1.04 | 100 | 1.47 | 98.69 | 1.45 | 100 | 3.71 | 91.20 |
| 30 | >100 | 19.48 | >100 | 21.11 | >100 | 31.90 | >100 | 0 |
| HCPT | 0.00364 | 84.68 | 0.00490 | 88.14 | 0.00127 | 96.71 | 0.147 | 100 |

TABLE 6

In vitro proliferation inhibiting effects of some samples of Formula (IIa) on human tumor cells

| | A549 | | Colo205 | | MDA-MB-435 | | HepG2 | |
|---|---|---|---|---|---|---|---|---|
| Compound No. | $IC_{50}$ (μg/mL) | 100 μg/mL IC % | $IC_{50}$ (μg/mL) | 100 μg/mL IC % | $IC_{50}$ (μg/mL) | 100 μg/mL IC % | $IC_{50}$ (μg/mL) | 100 μg/mL IC % |
| 31 | 1.72 | 93.62 | 1.20 | 88.35 | 1.83 | 86.09 | 0.746 | 90.60 |
| 32 | 8.58 | 92.32 | 7.45 | 92.85 | 10.73 | 96.48 | 6.92 | 70.03 |
| 33 | >100 | 40.55 | >100 | 29.31 | >100 | 27.19 | >100 | 4.57 |
| 34 | 6.58 | 100 | 6.82 | 99.54 | 19.78 | 100 | ≈100 | 49.68 |
| 35 | 19.04 | 72.15 | 3.89 | 100 | 3.88 | 100 | 20.09 | 100 |
| 36 | 78.22 | 61.01 | 28.58 | 79.84 | 28.86 | 83.69 | 61.69 | 59.74 |
| 37 | 58.58 | 61.64 | 36.76 | 69.37 | 41.01 | 70.26 | >100 | 24.95 |
| 38 | 13.16 | 100 | 18.77 | 95.16 | 9.37 | 100 | 22.97 | 88.62 |
| 39 | >100 | 47.81 | >100 | 13.12 | >100 | 14.88 | >100 | 22.39 |
| 40 | 3.25 | 86.70 | 3.16 | 100 | 1.52 | 100 | 11.51 | 100 |
| 41 | ≈100 | 49.27 | 0.632 | 83.62 | 0.703 | 77.77 | 3.36 | 85.01 |
| 42 | 8.03 | 87.75 | 1.27 | 100 | 3.12 | 100 | 3.77 | 100 |
| 43 | >100 | 4.26 | 34.21 | 87.42 | 83.60 | 53.07 | >100 | 9.73 |
| 44 | 1.42 | 94.74 | 0.346 | 92.66 | 0.014 | 78.20 | 1.93 | 84.59 |
| 45 | 37.85 | 62.84 | 16.76 | 66.89 | 7.86 | 72.95 | 6.27 | 84.31 |
| 46 | 12.52 | 68.78 | 22.18 | 87.44 | 0.267 | 85.86 | 12.02 | 90.77 |
| 47 | 10.60 | 87.20 | 1.66 | 88.74 | 5.30 | 100 | 8.33 | 64.50 |
| 48 | 23.76 | 79.61 | 11.75 | 89.59 | 12.36 | 100 | 60.46 | 62.67 |
| 49 | >100 | 28.48 | 69.03 | 50.06 | >100 | 48.01 | 21.05 | 59.34 |
| 50 | 3.59 | 85.91 | 15.89 | 76.93 | 1.12 | 89.80 | 3.71 | 36.98 |
| HCPT | 0.00364 | 84.68 | 0.00490 | 88.14 | 0.00127 | 96.71 | 0.147 | 100 |

It can be seen from Table 5 and 6 that the indenoquinolone compounds of the present invention showed good broad-spectrum anti-tumor activities on human lung cancer, colon cancer, breast cancer and liver cancer. Particularly, some compounds showed better cytotoxic activity on human hepatoma cell lines. Therefore, it is expected that the compounds of the present invention have good prospects for development.

Example 52

Topoisomerase I Inhibitory Activity Test

The topoisomerase I inhibitory activity of the compounds synthesized in examples was detected by using literature method (Dexheimer, T S, Pommier Y. DNA Cleavage assay for the identification of topoisomerase the I Inhibitors Nature the Protocols, 2008, 3: 1736-50). It can be found that they have good Topoisomerase I inhibitory activities in the range of 0.01-100 uM, wherein, the inhibitory activity of camptothecin as the positive control drug was ++++, that of some compounds of the invention, for example 15, was ++++, which is equivalent to that of camptothecin. The inhibitory activity of some compounds of the invention, for example 5, 7, 11, 13, 14, 42, and 46, was +++, and other compounds also showed various degree of inhibiting enzyme activity.

Example 53

The Anti-Tumor Activity Test In Vivo

The activities of some compounds in vivo in the nude mouse model of human lung cancer cell line A549 were detected by using literature methods (WEI Hong. Medical Experiments Zoology. 2nd edition. Chengdu: Sichuan Science and Technology Press, 2001: 595-596). The results showed that compounds 1, 6, 14, 20, 31 and 46 of the present invention with the dose of 1-200 mg/kg weight have good anti-tumor activity in vivo.

Example 54

Pharmaceutical Composition

Formulation:

| | |
|---|---|
| Compound 7 in Example | 20.0 g |
| Starch | 80.0 g |
| Lactose | 60.0 g |
| Microcrystalline cellulose | 35.0 g |
| 10% polyvinylpyrrolidone solution in ethanol | appropriate amount |
| Magnesium stearate | 0.5 g |

1000 capsules in total were prepared.

Compound 7 and various excipients were sifted through 80 mesh sieve. Each component was weighted according to the formulation. 10% polyvinyl pyrrolidone solution in ethanol was used as a binder. Appropriate particles were prepared with a 16 mesh sieve. The particles were dried at 65° C., and granulated with 14 mesh sieve. Magnesium stearate was added and mixed uniformly. The particle content was measured, the loaded amount was calculated, and the particles were filled into the capsules.

The compounds of the present invention have broad-spectrum anti-tumor activities. Especially, some of the compounds have strong anti-tumor activities on the liver cancer, lung cancer, colon cancer, and breast cancer, and are valuable for development. The indenoquinolone compounds of the present invention represent a class of compounds having novel structures and anti-tumor activities, which opened up a new way and direction for further research and development of new anticancer drugs.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed is:
1. An indenoquinolone compound of general formula (I), or the pharmaceutically acceptable salt, solvate or polymorph thereof:

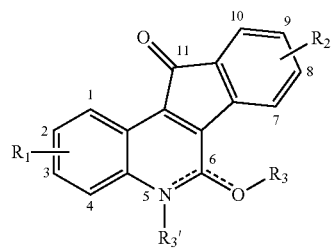

(A)

wherein, $R_1$ is located at one or two positions of 2- and 3-position; and/or $R_2$ is located at one or two positions of 8- and 9-position,
$R_1$ is any one of the following groups: a) a hydrogen; b) a C1-8 straight-chain or branched alkyloxy; c) a halogen; and/or
$R_2$ is any one of the following groups: a) a hydrogen; b) a C1-8 straight-chain or branched alkyloxy; c) a halogen;
$R_1$ is —$(CH_2)_m R_4$, wherein m is 2-3, $R_4$ is a saturated or unsaturated 5-6 membered nitrogen-containing heterocycle, or $NR_5R_6$, wherein $R_5$ is any one of the following groups: a) a hydrogen; b) an unsubstituted C1-8 straight-chain or branched alkyl; $R_6$ is any one of the following groups: as hydrogen; b) an unsubstituted C1-8 straight-chain or branched alkyl.

2. The compound according to claim 1, wherein, the compound is selected from the group consisting of compounds 1-29 of formula (Ia),

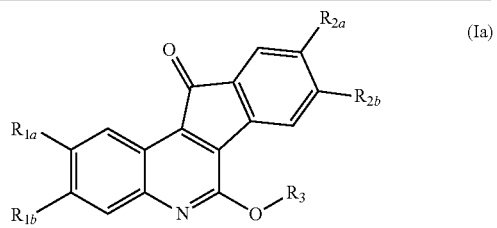

(Ia)

| Compound No. | $R_{1a}$ | $R_{1b}$ | $R_{2a}$ | $R_{2b}$ | $R_3$ |
|---|---|---|---|---|---|
| 1 | H | H | OCH$_3$ | H | CH$_2$CH$_2$N(CH$_3$)$_2$ |
| 2 | H | H | OCH$_3$ | H | CH$_2$CH$_2$N(CH$_2$CH$_3$)$_2$ |

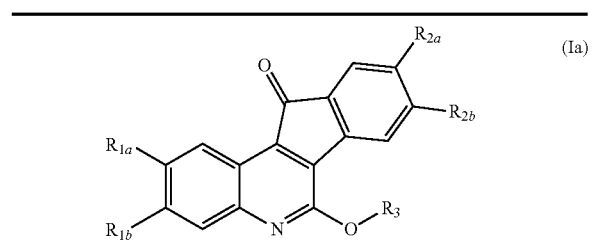

(Ia)

| Compound No. | R$_{1a}$ | R$_{1b}$ | R$_{2a}$ | R$_{2b}$ | R$_3$ |
|---|---|---|---|---|---|
| 3 | H | H | OCH$_3$ | H | CH$_2$CH$_2$N-pyrrolidine |
| 4 | H | H | OCH$_3$ | H | CH$_2$CH$_2$N-imidazole |
| 5 | H | H | OCH$_3$ | H | CH$_2$CH$_2$N-morpholine |
| 6 | H | H | OCH$_3$ | H | CH$_2$CH$_2$CH$_2$N(CH$_3$)$_2$ |
| 7 | H | H | Cl | H | CH$_2$CH$_2$N(CH$_3$)$_2$ |
| 8 | H | H | Cl | H | CH$_2$CH$_2$N(CH$_2$CH$_3$)$_2$ |
| 9 | H | H | Cl | H | CH$_2$CH$_2$N-pyrrolidine |
| 10 | H | H | Cl | H | CH$_2$CH$_2$N-imidazole |
| 11 | H | H | Cl | H | CH$_2$CH$_2$N-piperidine |
| 12 | H | H | Cl | H | CH$_2$CH$_2$CH$_2$N(CH$_3$)$_2$ |
| 13 | OCH$_3$ | H | OCH$_3$ | H | CH$_2$CH$_2$N(CH$_3$)$_2$ |
| 14 | OCH$_3$ | H | OCH$_3$ | H | CH$_2$CH$_2$N(CH$_2$CH$_3$)$_2$ |
| 15 | OCH$_3$ | H | OCH$_3$ | H | CH$_2$CH$_2$N-piperidine |
| 16 | OCH$_3$ | H | OCH$_3$ | H | CH$_2$CH$_2$CH$_2$N(CH$_3$)$_2$ |
| 17 | OCH$_3$ | H | H | OCH$_3$ | CH$_2$CH$_2$N(CH$_3$)$_2$ |
| 18 | OCH$_3$ | H | Br | H | CH$_2$CH$_2$N-pyrrolidine |
| 19 | OCH$_3$ | H | Br | H | CH$_2$CH$_2$N-imidazole |
| 20 | OCH$_3$ | OCH$_3$ | OCH$_3$ | H | CH$_2$CH$_2$N(CH$_3$)$_2$ |
| 21 | OCH$_3$ | OCH$_3$ | OCH$_3$ | H | CH$_2$CH$_2$N(CH$_2$CH$_3$)$_2$ |
| 22 | OCH$_3$ | OCH$_3$ | OCH$_3$ | H | CH$_2$CH$_2$N-pyrrolidine |
| 23 | OCH$_3$ | OCH$_3$ | OCH$_3$ | H | CH$_2$CH$_2$N-morpholine |

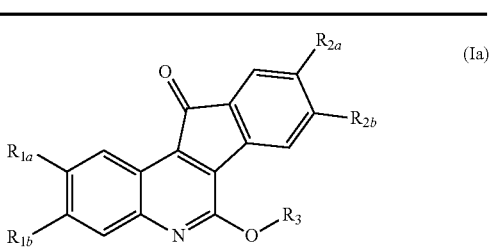

(Ia)

| Compound No. | R$_{1a}$ | R$_{1b}$ | R$_{2a}$ | R$_{2b}$ | R$_3$ |
|---|---|---|---|---|---|
| 24 | OCH$_3$ | OCH$_3$ | OCH$_3$ | H | CH$_2$CH$_2$N-piperidine |
| 25 | OCH$_3$ | OCH$_3$ | OCH$_3$ | H | CH$_2$CH$_2$CH$_2$N(CH$_3$)$_2$ |
| 26 | OCH$_3$ | OCH$_3$ | Cl | H | CH$_2$CH$_2$N(CH$_3$)$_2$ |
| 27 | OCH$_3$ | OCH$_3$ | Cl | H | CH$_2$CH$_2$N-imidazole |
| 28 | OCH$_3$ | OCH$_3$ | Cl | H | CH$_2$CH$_2$N-morpholine |
| 29 | OCH$_3$ | OCH$_3$ | Cl | H | CH$_2$CH$_2$CH$_2$N(CH$_3$)$_2$ |

3. A composition, comprising the compound or the pharmaceutically acceptable salts thereof of claim 1, and a pharmaceutically acceptable carrier.

4. A method for inhibiting topoisomerase I, comprising contacting topoisomerase I with the compound of claim 1.

5. The method of claim 4, wherein the method is an in vitro method.

6. A method for inhibiting topoisomerase I in a subject, comprising administering the compound of claim 1 to the subject in need thereof.

7. A method for treating colon, breast, lung, or liver cancer in a subject, comprising administering the compound of claim 1 to the subject in need thereof.

8. A method for preparing the compound of claim 1, comprising reacting the compound of formula VII with R$_3$X or a salt thereof in an inert solvent under alkaline conditions, thereby forming the compound of formula I and II,

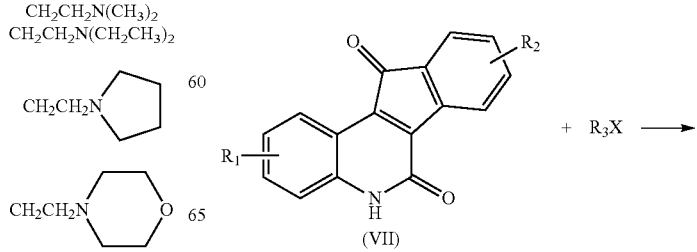

-continued
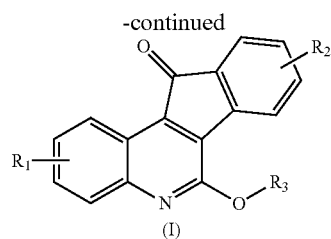
(I)
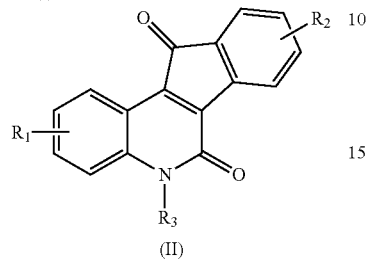
(II)
wherein, $R_1$, $R_2$, and $R_3$ are defined as in claim 1, X is a leaving group, and the salt of $R_3X$ is an inorganic acid salt or an organic acid salt.
* * * * *